(12) United States Patent
Biedermann et al.

(10) Patent No.: US 11,083,589 B2
(45) Date of Patent: Aug. 10, 2021

(54) MULTI-WALLED PLACEHOLDER

(71) Applicant: BIEDERMANN TECHNOLOGIES GMBH & CO. KG, Donaueschingen (DE)

(72) Inventors: Lutz Biedermann, VS-Villingen (DE); Wilfried Matthis, Weisweil (DE); Helmar Rapp, Deisslingen (DE)

(73) Assignee: BIEDERMANN TECHNOLOGIES GMBH & CO. KG, Donaeuschingen (DE)

(*) Notice: Subject to any disclaimer, the term of this patent is extended or adjusted under 35 U.S.C. 154(b) by 0 days.

(21) Appl. No.: 16/166,839

(22) Filed: Oct. 22, 2018

(65) Prior Publication Data

US 2019/0159908 A1    May 30, 2019

Related U.S. Application Data

(63) Continuation of application No. 15/728,405, filed on Oct. 9, 2017, now Pat. No. 10,130,485, which is a
(Continued)

(51) Int. Cl.
*A61F 2/44* (2006.01)
*G02F 1/1343* (2006.01)
(Continued)

(52) U.S. Cl.
CPC ............... *A61F 2/442* (2013.01); *A61F 2/44* (2013.01); *A61F 2/4465* (2013.01); *G02F 1/13439* (2013.01); *G02F 1/13458* (2013.01); *A61B 17/7001* (2013.01); *A61B 17/72* (2013.01); *A61B 17/80* (2013.01); *A61F 2/30767* (2013.01); *A61F 2/4455* (2013.01); *A61F 2002/2825* (2013.01);
(Continued)

(58) Field of Classification Search
CPC .................. A61F 2/4455; A61F 2/446; A61F 2002/4475; A61F 2002/448; A61F 2002/4495
USPC ............................................ 623/17.11–17.16
See application file for complete search history.

(56) References Cited

U.S. PATENT DOCUMENTS 4,820,305 A    4/1989   Harms et al.
5,211,664 A    5/1993   Tepic et al.
(Continued)

FOREIGN PATENT DOCUMENTS

DE    44 23 257 C2    1/1996
DE    195 04 867 C1   2/1996
(Continued)

*Primary Examiner* — Matthew J Lawson
(74) *Attorney, Agent, or Firm* — Lewis Roca Rothgerber Christie LLP

(57) ABSTRACT

A placeholder for vertebrae or vertebral discs includes a tubular body, which along its jacket surface has a plurality of breakthroughs or openings for over-growth with adjacent tissue. The placeholder includes at least a second tubular body provided with a plurality of breakthroughs and openings at least partially inside the first tubular body. The first and second tubular bodies can have different cross-sectional shapes, can be are arranged inside one another by press fit or force fit or can be connected to each other via connecting pins and arranged side by side to one another in the first body.

29 Claims, 19 Drawing Sheets

Related U.S. Application Data continuation of application No. 15/012,827, filed on Feb. 1, 2016, now Pat. No. 9,814,595, which is a continuation of application No. 13/914,471, filed on Jun. 10, 2013, now Pat. No. 9,254,199, which is a continuation of application No. 11/645,228, filed on Dec. 22, 2006, now abandoned.

(60) Provisional application No. 60/808,028, filed on May 23, 2006, provisional application No. 60/753,854, filed on Dec. 23, 2005.

(51) Int. Cl.
| | | |
|---|---|---|
| *G02F 1/1345* | (2006.01) | |
| *A61B 17/70* | (2006.01) | |
| *A61B 17/72* | (2006.01) | |
| *A61B 17/80* | (2006.01) | |
| *A61F 2/30* | (2006.01) | |
| *A61F 2/28* | (2006.01) | |
| *H01L 29/45* | (2006.01) | |
| *H01L 29/49* | (2006.01) | |
| *H01L 27/12* | (2006.01) | |

(52) U.S. Cl.
CPC .............. *A61F 2002/3055* (2013.01); *A61F 2002/3097* (2013.01); *A61F 2002/30115* (2013.01); *A61F 2002/30126* (2013.01); *A61F 2002/30131* (2013.01); *A61F 2002/30133* (2013.01); *A61F 2002/30143* (2013.01); *A61F 2002/30146* (2013.01); *A61F 2002/30148* (2013.01); *A61F 2002/30153* (2013.01); *A61F 2002/30154* (2013.01); *A61F 2002/30156* (2013.01); *A61F 2002/30235* (2013.01); *A61F 2002/30433* (2013.01); *A61F 2002/30451* (2013.01); *A61F 2002/30485* (2013.01); *A61F 2002/30492* (2013.01); *A61F 2002/30507* (2013.01); *A61F 2002/30593* (2013.01); *A61F 2002/30601* (2013.01); *A61F 2002/30672* (2013.01); *A61F 2002/30787* (2013.01); *A61F 2002/30841* (2013.01); *A61F 2002/30912* (2013.01); *A61F 2220/0025* (2013.01); *A61F 2220/0041* (2013.01); *A61F 2220/0058* (2013.01); *A61F 2230/0006* (2013.01); *A61F 2230/0008* (2013.01); *A61F 2230/0013* (2013.01); *A61F 2230/0015* (2013.01); *A61F 2230/0017* (2013.01); *A61F 2230/0019* (2013.01); *A61F 2230/0021* (2013.01); *A61F 2230/0023* (2013.01); *A61F 2230/0069* (2013.01); *A61F 2310/00023* (2013.01); *A61F 2310/00796* (2013.01); *H01L 27/12* (2013.01); *H01L 27/124* (2013.01); *H01L 29/458* (2013.01); *H01L 29/4908* (2013.01)

(56) References Cited

U.S. PATENT DOCUMENTS

| | | | |
|---|---|---|---|
| 5,571,192 | A | 11/1996 | Schönhöffer |
| 5,972,031 | A | 10/1999 | Biedermann et al. |
| 6,015,436 | A | 1/2000 | Schönhöffer |
| 6,176,881 | B1 | 1/2001 | Schar |
| 6,193,755 | B1 | 2/2001 | Metz-Stavenhagen et al. |
| 6,193,756 | B1 | 2/2001 | Studer et al. |
| 6,200,348 | B1 | 3/2001 | Biedermann et al. |
| 6,206,924 | B1 | 3/2001 | Timm |
| 6,447,543 | B1 | 9/2002 | Studer |
| 6,616,695 | B1 | 9/2003 | Crozet et al. |
| 6,743,256 | B2 | 6/2004 | Mason |
| 6,776,798 | B2 | 8/2004 | Camino et al. |
| 6,783,547 | B2 | 8/2004 | Castro |
| 6,866,682 | B1 | 3/2005 | An et al. |
| 6,923,830 | B2 | 8/2005 | Michelson |
| 7,029,498 | B2 | 4/2006 | Boehm et al. |
| 7,056,343 | B2 | 6/2006 | Schäfer et al. |
| 8,920,502 | B1 | 12/2014 | Muhanna |
| 2001/0014826 | A1 | 8/2001 | Biedermann |
| 2002/0068978 | A1 | 6/2002 | Camino |
| 2002/0082696 | A1 | 6/2002 | Harms |
| 2002/0138142 | A1* | 9/2002 | Castro .............. A61F 2/4465 623/17.11 |
| 2002/0161441 | A1 | 10/2002 | Lang et al. |
| 2003/0078660 | A1 | 4/2003 | Clifford et al. |
| 2003/0083746 | A1 | 5/2003 | Kuslich |
| 2003/0105527 | A1 | 6/2003 | Bresina |
| 2003/0181980 | A1 | 9/2003 | Berry et al. |
| 2003/0191535 | A1 | 10/2003 | Castro |
| 2004/0010315 | A1 | 1/2004 | Song |
| 2004/0049270 | A1 | 3/2004 | Gewirtz |
| 2004/0049271 | A1 | 3/2004 | Biedermann et al. |
| 2004/0098128 | A1 | 5/2004 | Biedermann et al. |
| 2004/0172129 | A1 | 9/2004 | Schafer |
| 2004/0210312 | A1 | 10/2004 | Neumann |
| 2004/0225360 | A1 | 11/2004 | Malone |
| 2004/0259972 | A1 | 12/2004 | Ringeisen |
| 2005/0015154 | A1 | 1/2005 | Lindsey et al. |
| 2005/0033425 | A1 | 2/2005 | Schwab |
| 2005/0090898 | A1 | 4/2005 | Berry et al. |
| 2005/0159814 | A1 | 7/2005 | Karahalios |
| 2005/0234550 | A1 | 10/2005 | Metz-Stavenhagen |
| 2006/0074490 | A1 | 4/2006 | Sweeney |
| 2006/0241762 | A1 | 10/2006 | Kraus |
| 2009/0036985 | A1 | 2/2009 | Whiting |
| 2012/0265303 | A1 | 10/2012 | Refai |
| 2013/0053965 | A1 | 2/2013 | Metz-Stavenhagen |

FOREIGN PATENT DOCUMENTS

| | | |
|---|---|---|
| DE | 195 09 317 A1 | 9/1996 |
| DE | 196 22 827 A1 | 12/1997 |
| DE | 198 04 765 A1 | 8/1999 |
| DE | 101 38 079 A1 | 2/2003 |
| DE | 102 10 214 B4 | 9/2003 |
| DE | 697 19 431 T2 | 9/2003 |
| DE | 600 15 879 T2 | 3/2005 |
| DE | 103 57 926 B3 | 9/2005 |
| EP | 0268115 A1 | 5/1988 |
| EP | 0 904 751 A1 | 3/1999 |
| EP | 0968692 A1 | 1/2000 |
| EP | 1080703 A2 | 3/2001 |
| EP | 1350489 A2 | 10/2003 |
| EP | 1 361 840 B1 | 11/2003 |
| EP | 1 430 857 A1 | 6/2004 |
| GB | 2364643 A | 2/2002 |
| JP | 2002-501783 A | 1/2002 |
| JP | 2004-275764 A | 10/2004 |
| JP | 2005-538749 A | 12/2005 |
| JP | 3861229 B2 | 10/2006 |
| TW | I243052 | 11/2005 |
| WO | WO 01/72246 A1 | 10/2001 |
| WO | WO 02/064059 A2 | 8/2002 |
| WO | WO 2004/008999 A1 | 1/2004 |
| WO | WO 2004/019827 A1 | 3/2004 |
| WO | WO 2004/108023 A1 | 12/2004 |
| WO | WO 2005/013861 A1 | 2/2005 |
| WO | WO 2005/0234550 | 10/2005 |

* cited by examiner

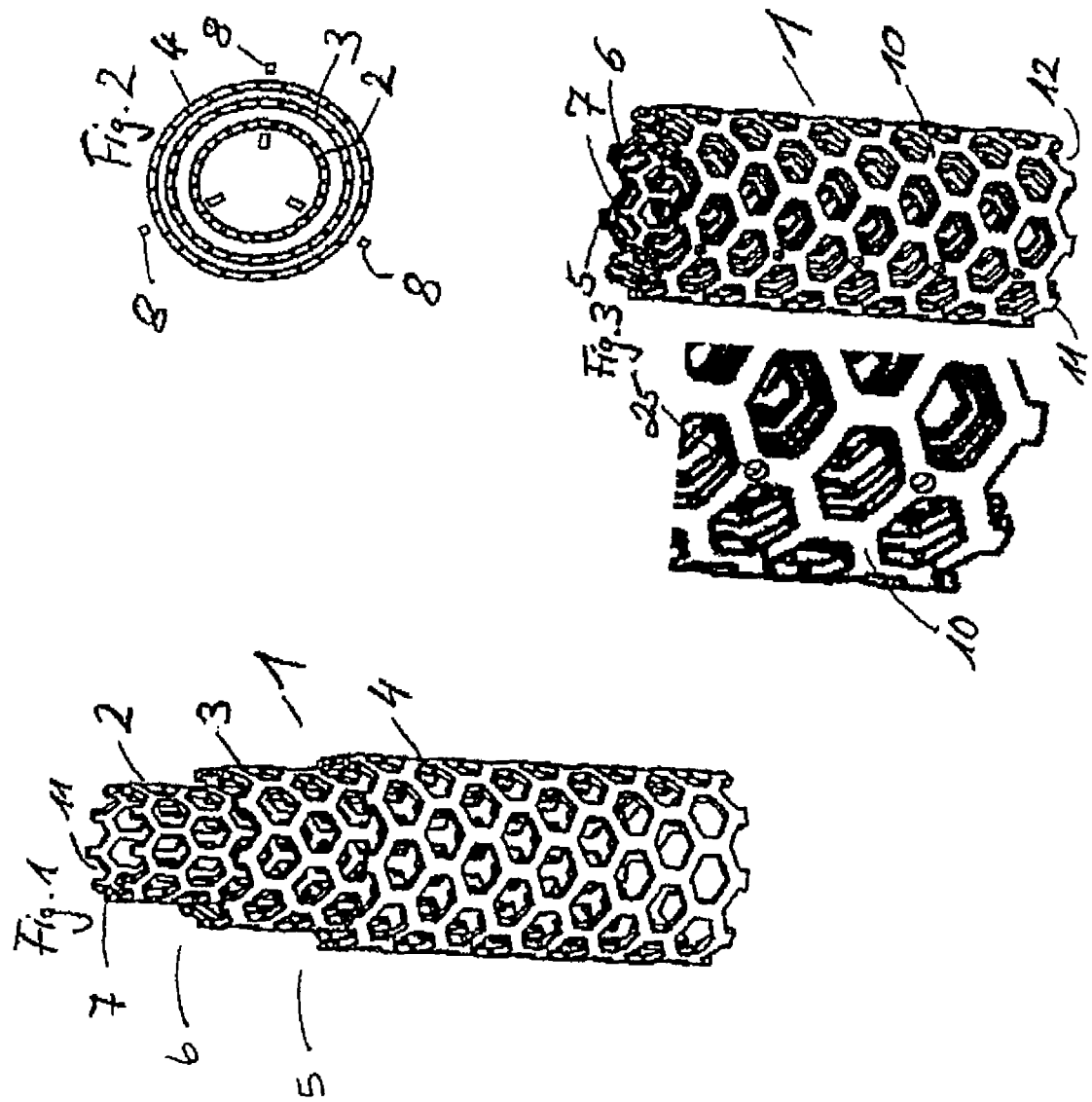

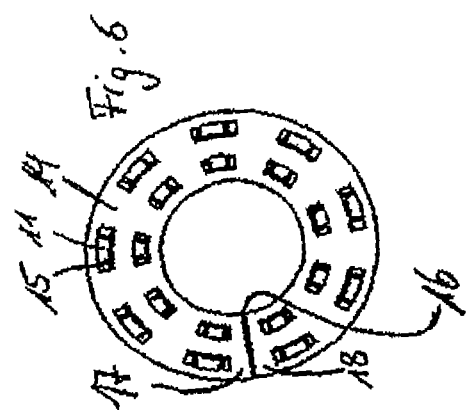
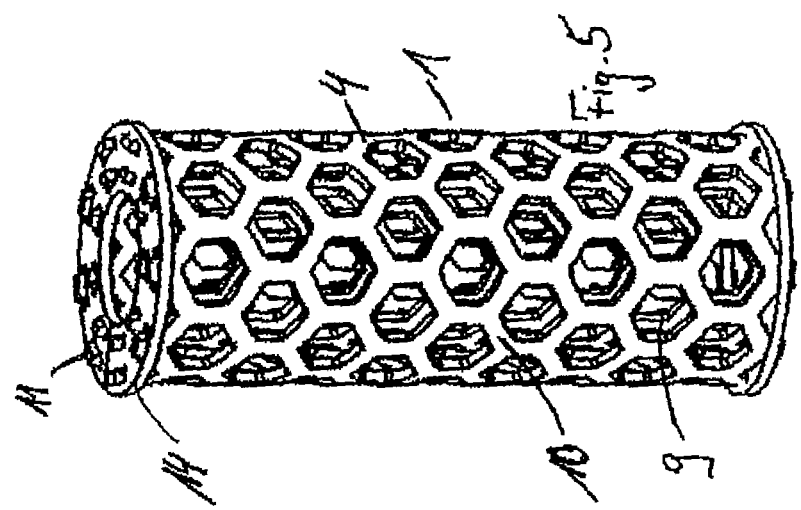
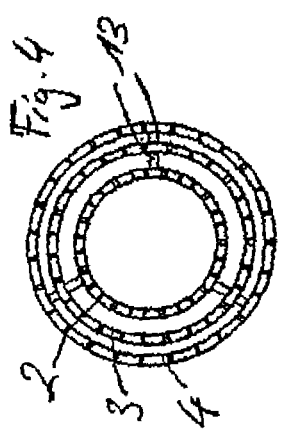

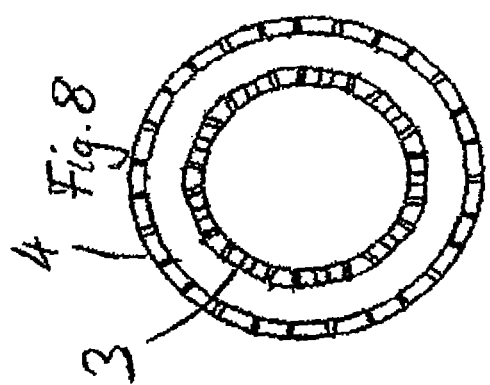
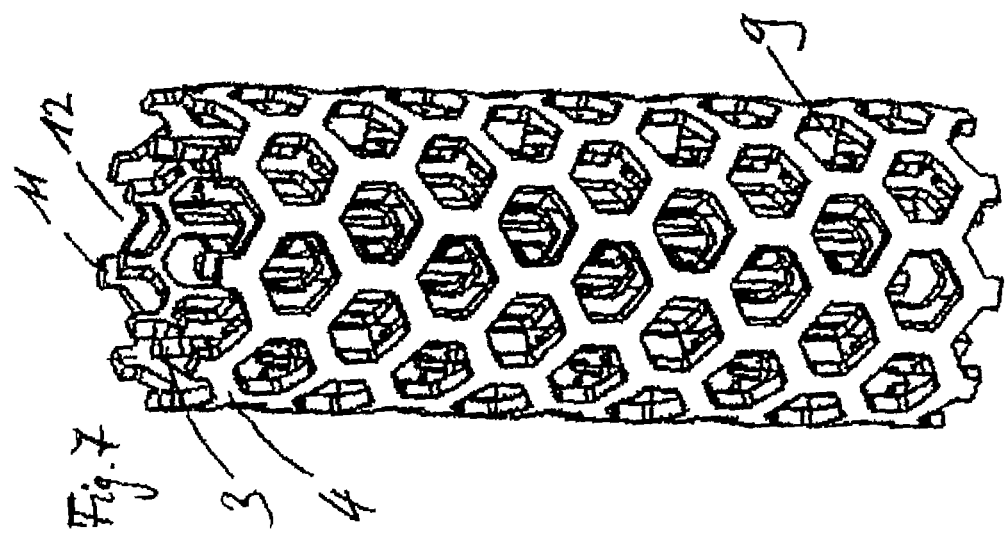

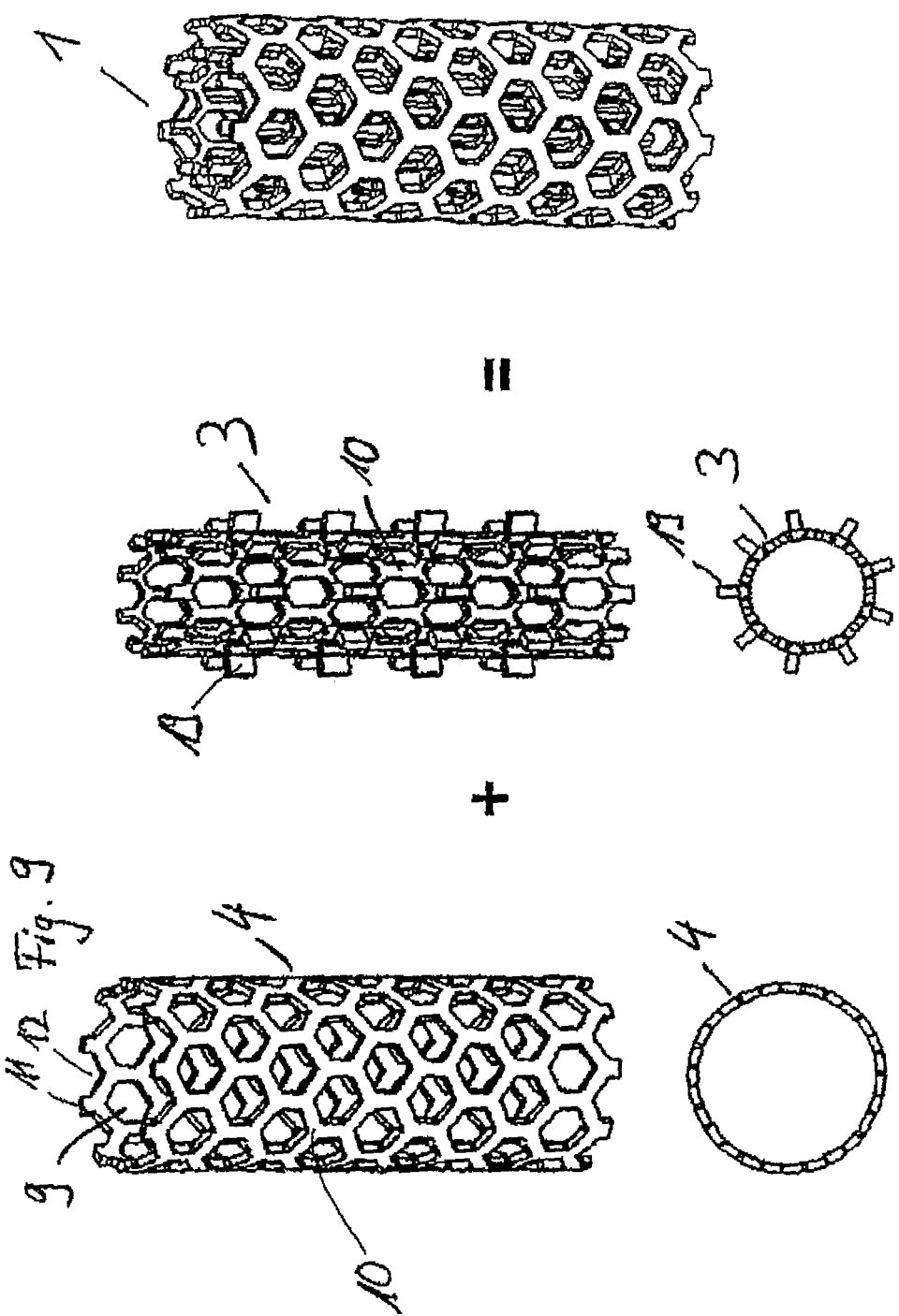

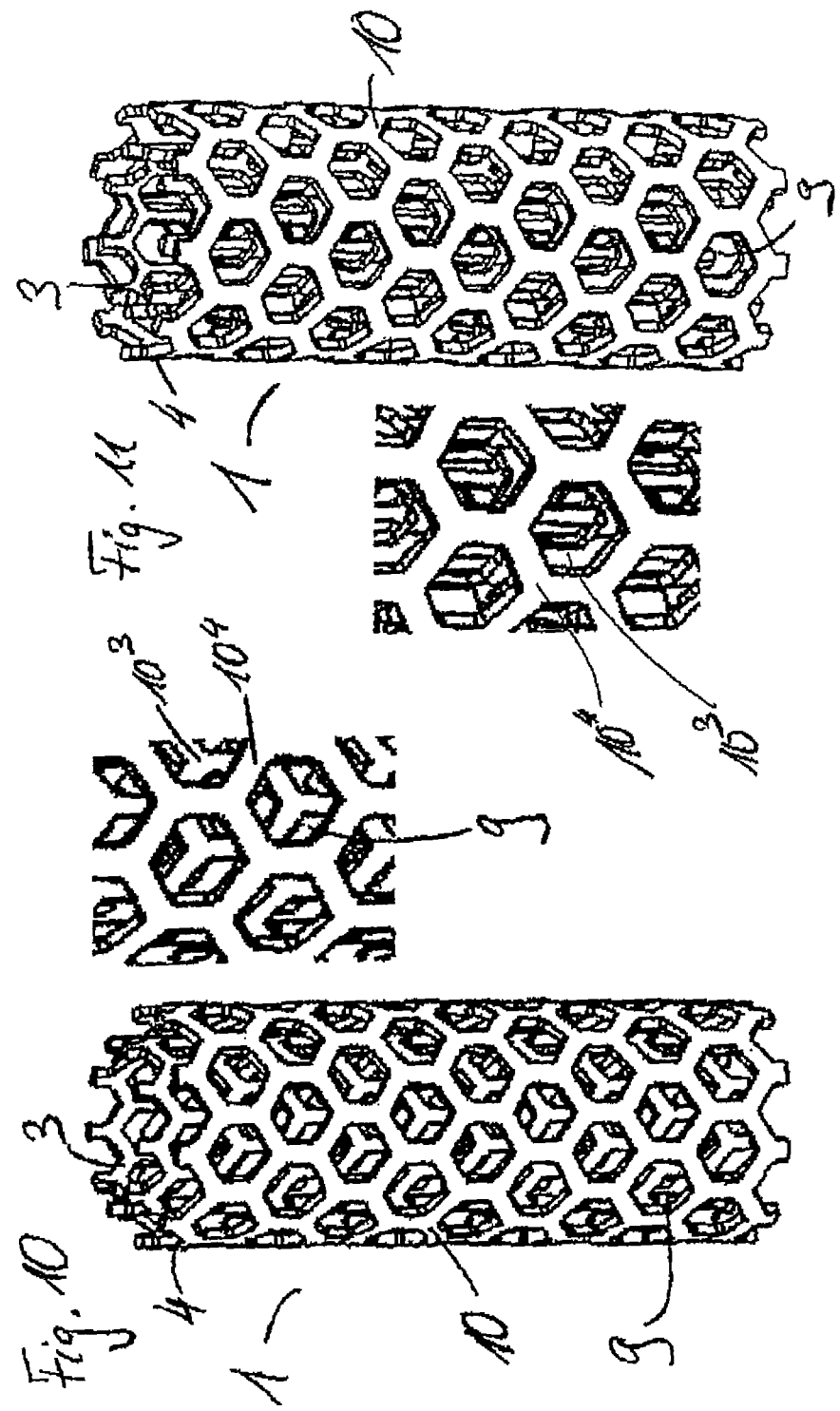

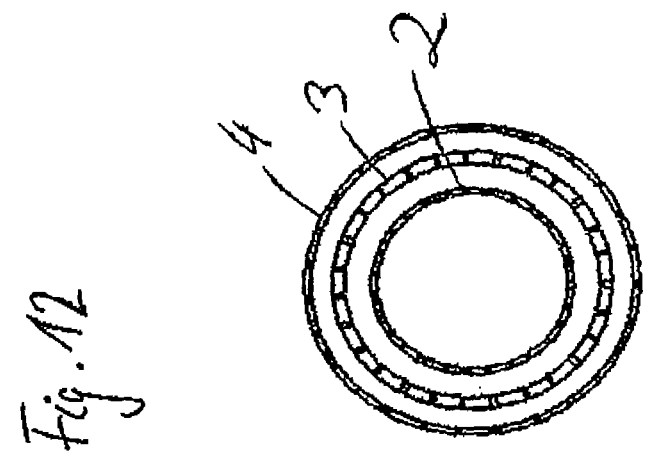
Fig. 12
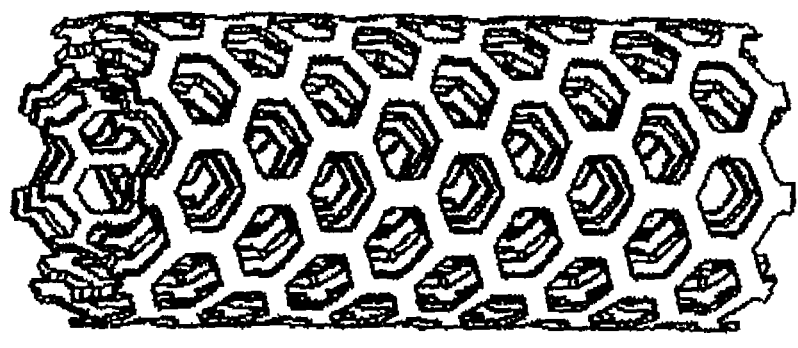

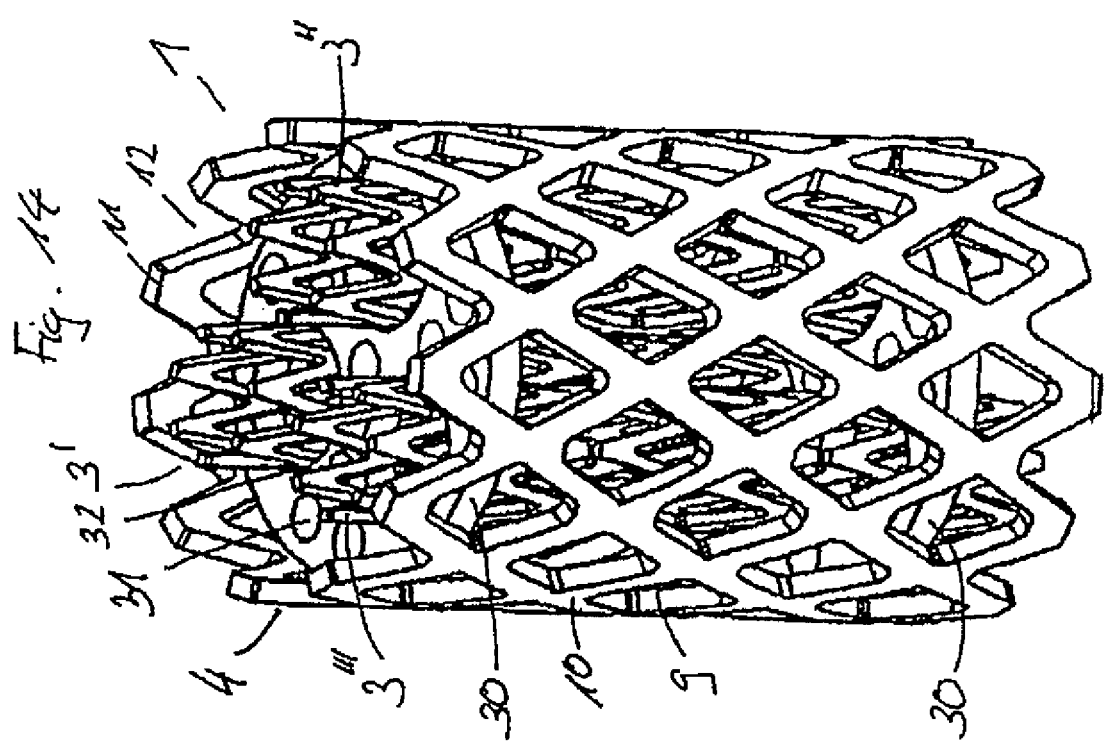

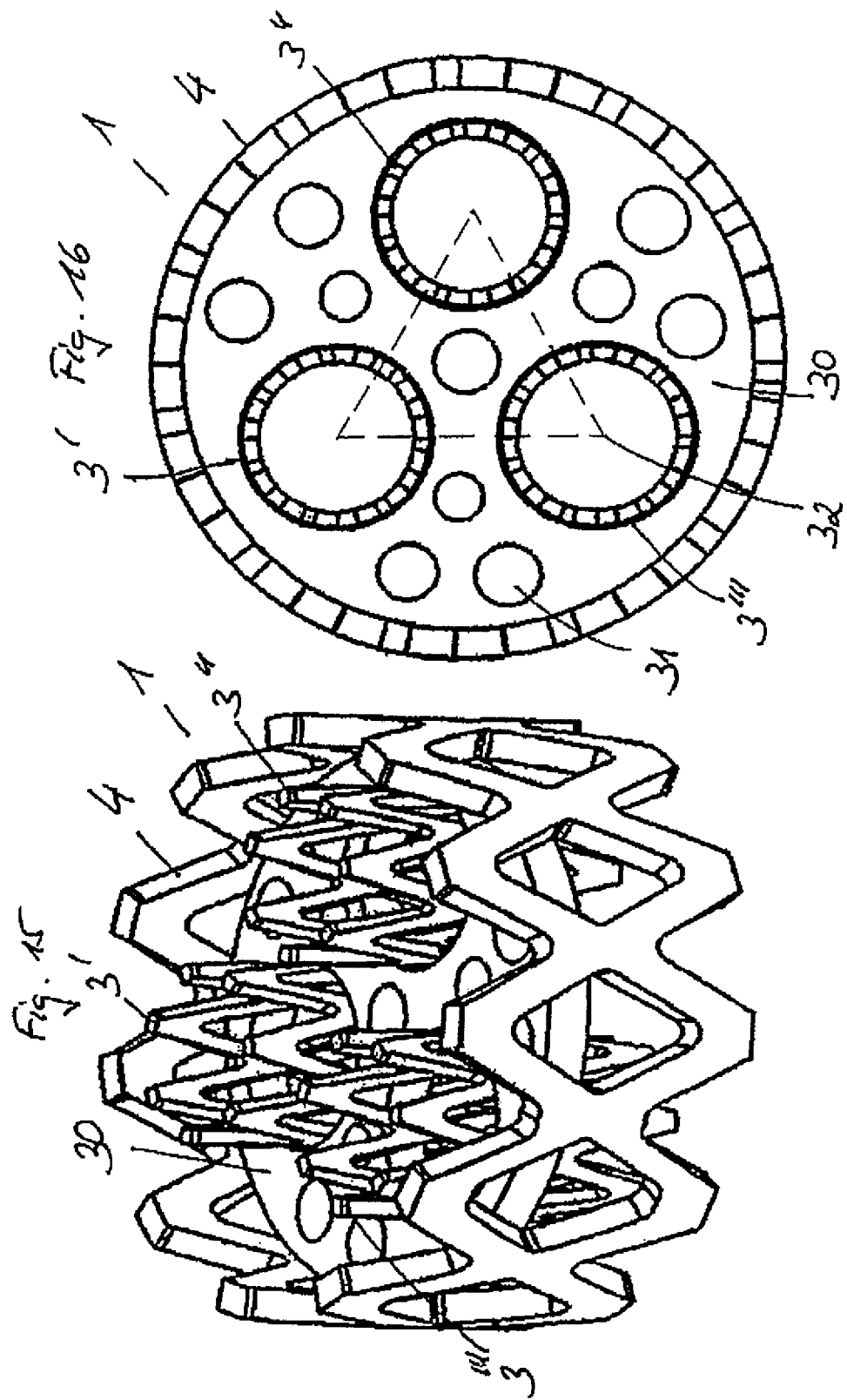

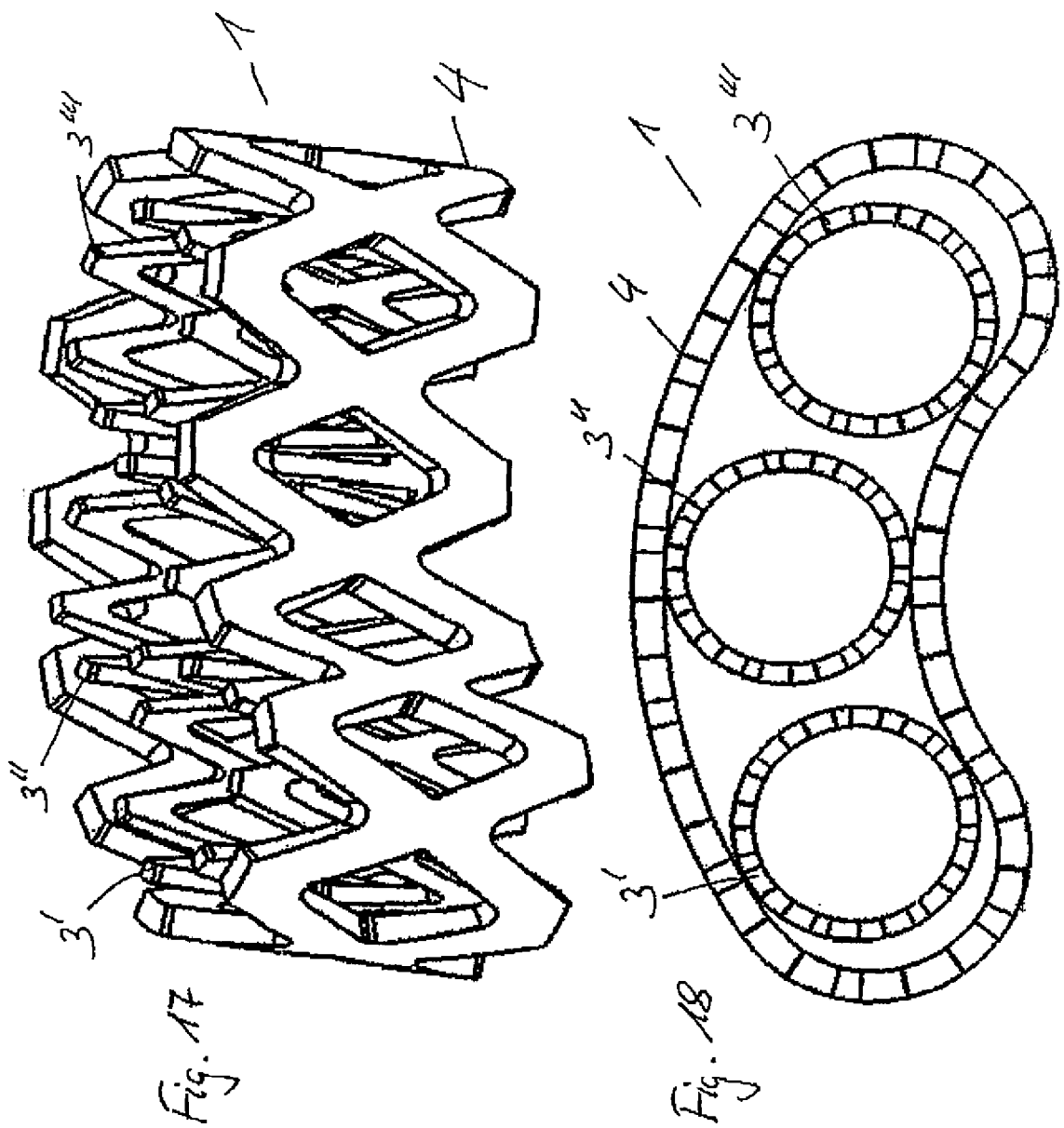

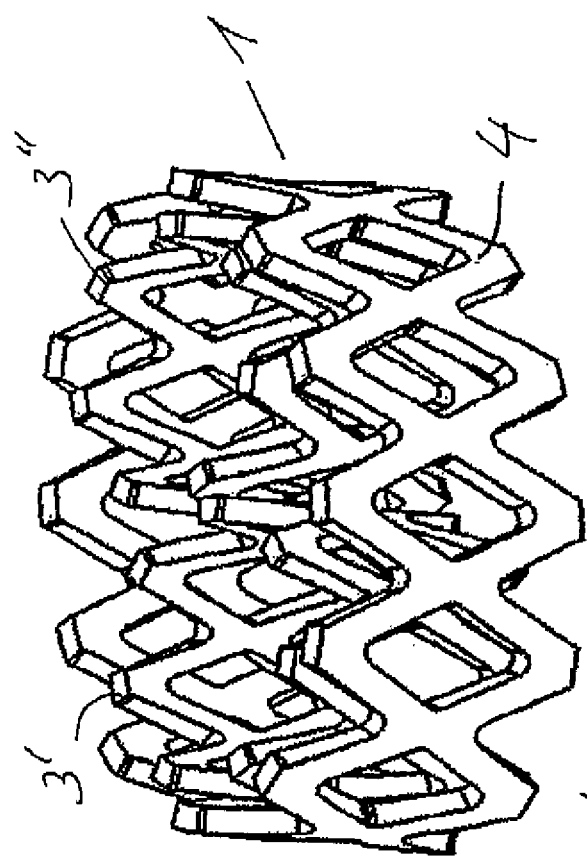
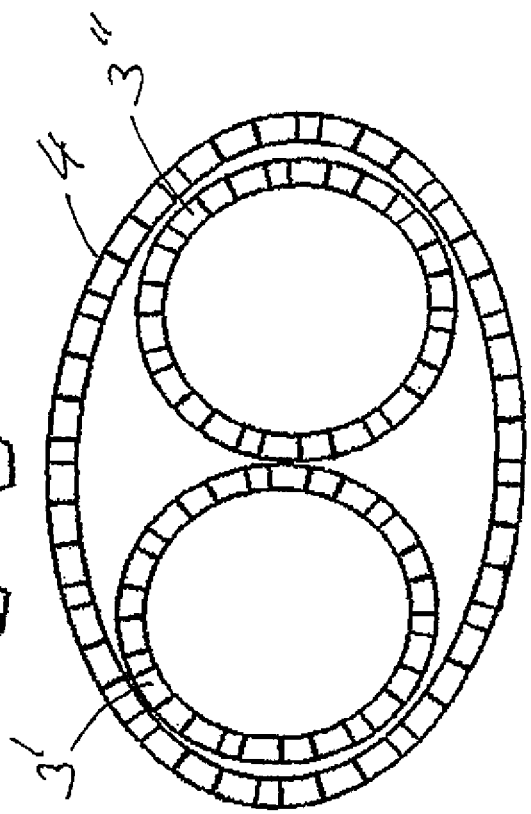
Fig. 19
Fig. 20

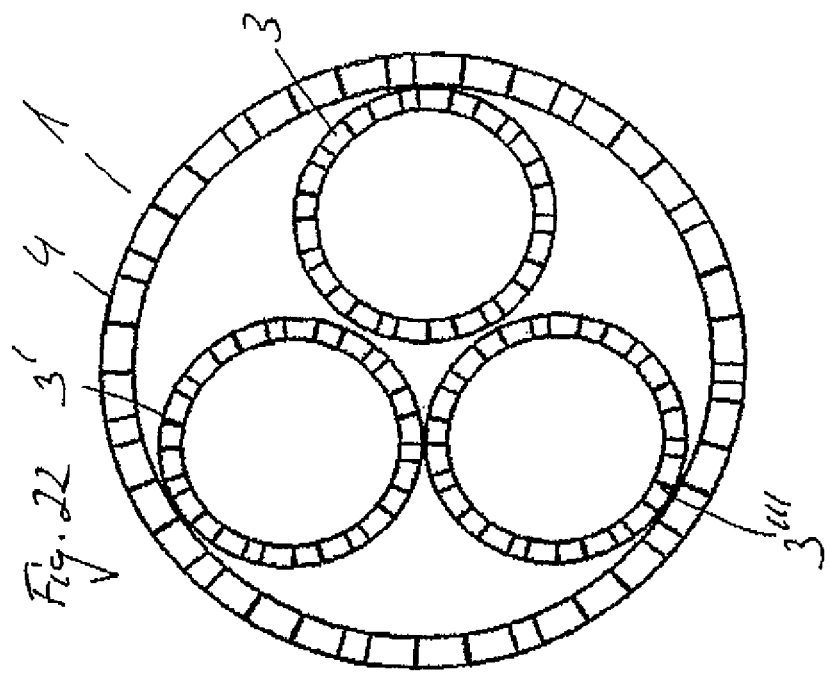
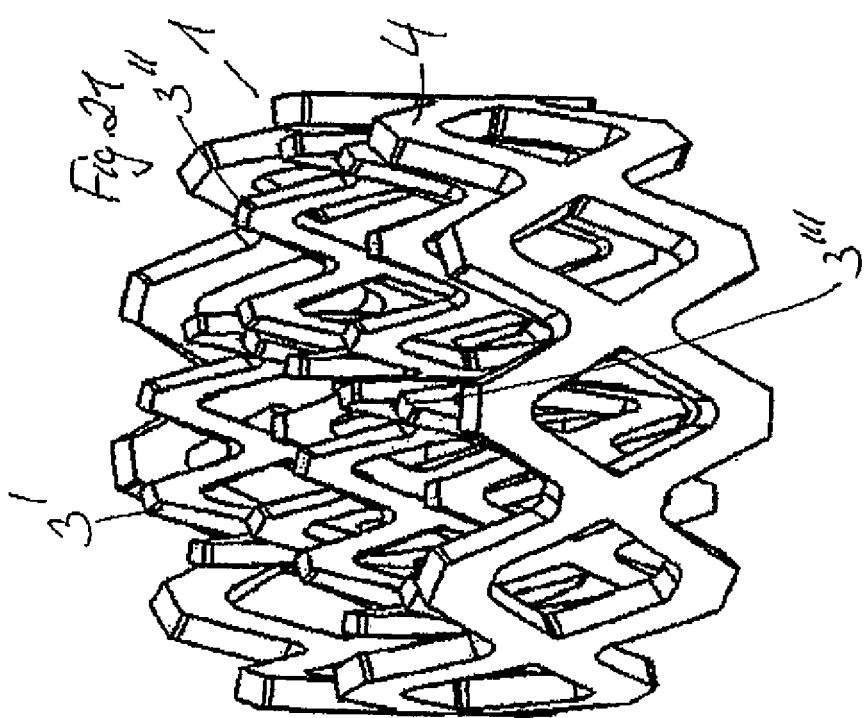

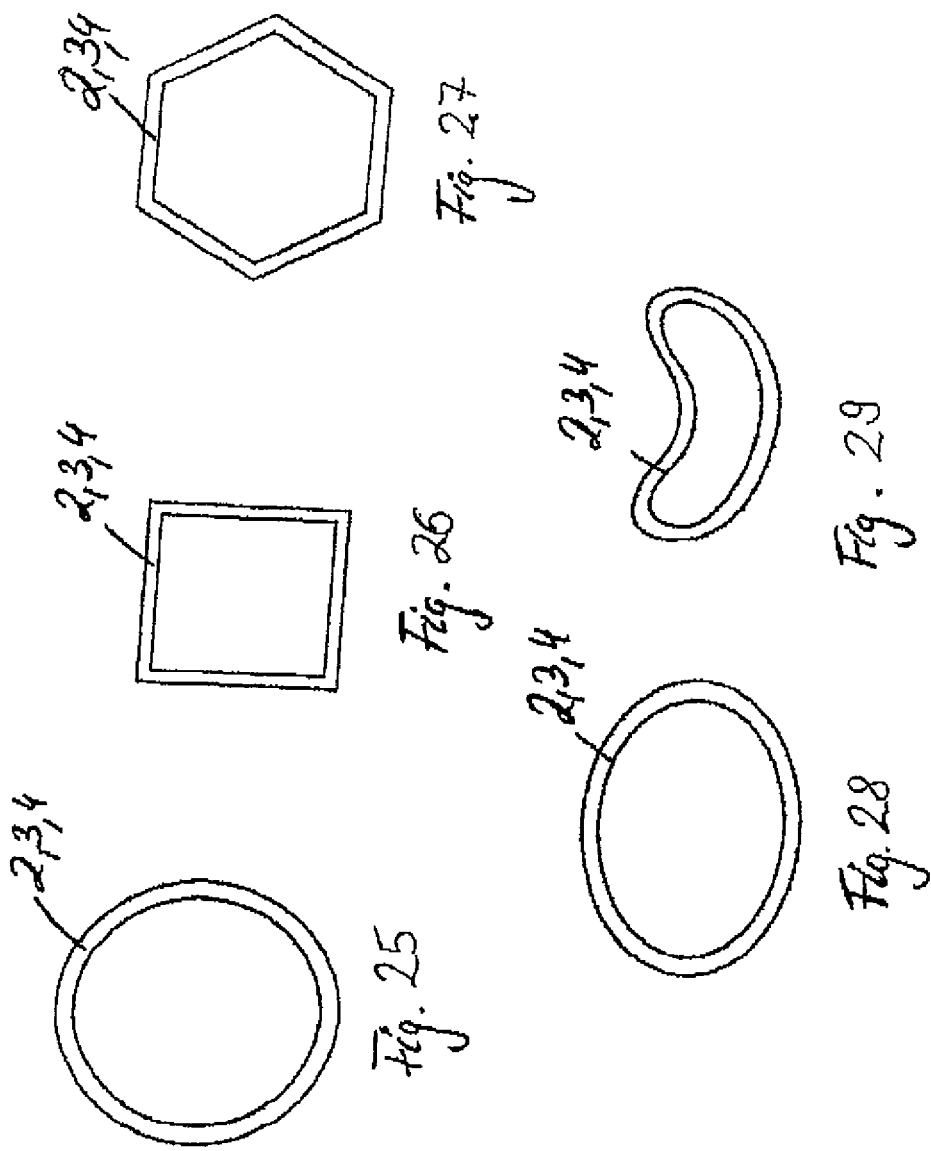

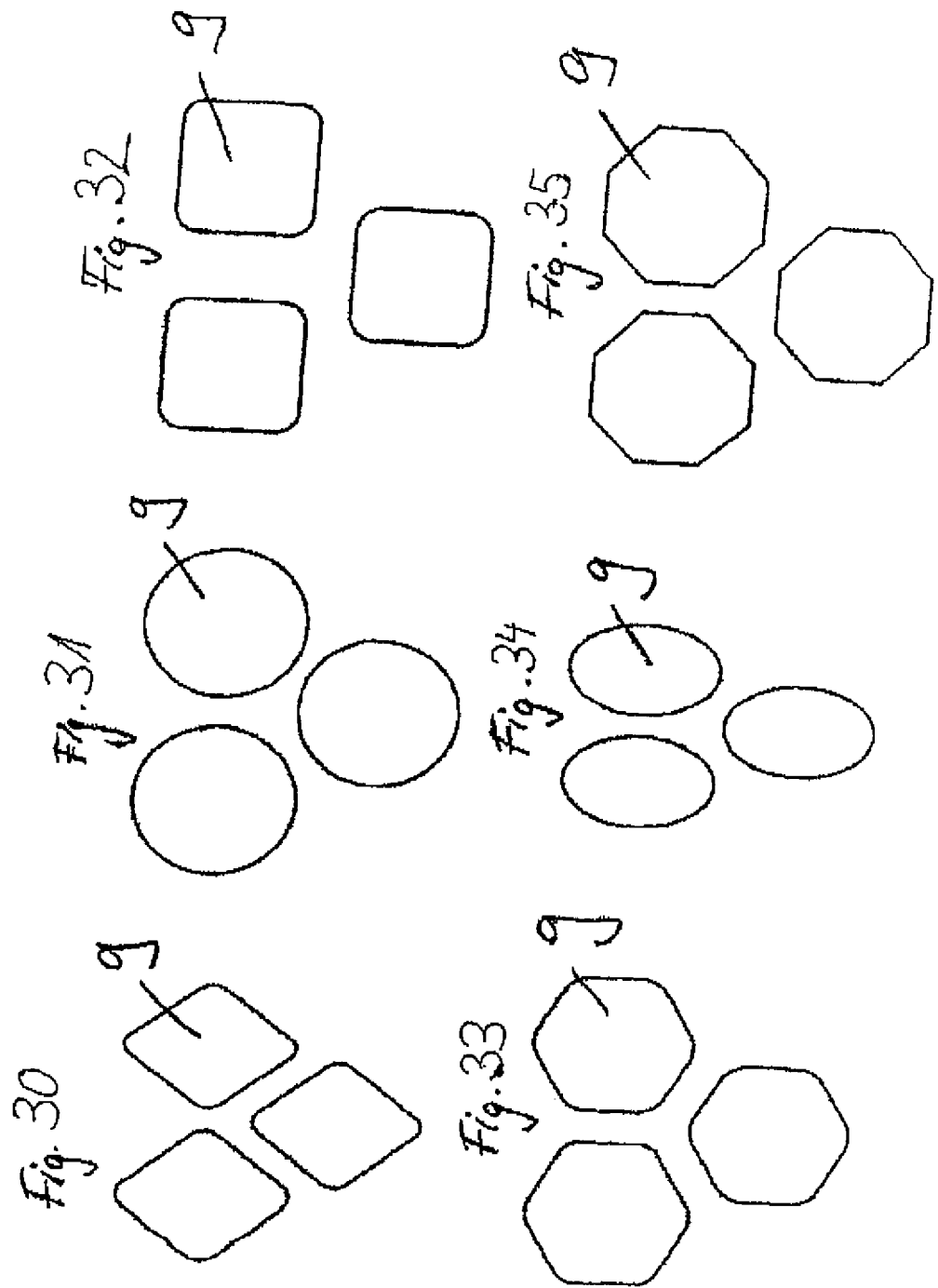

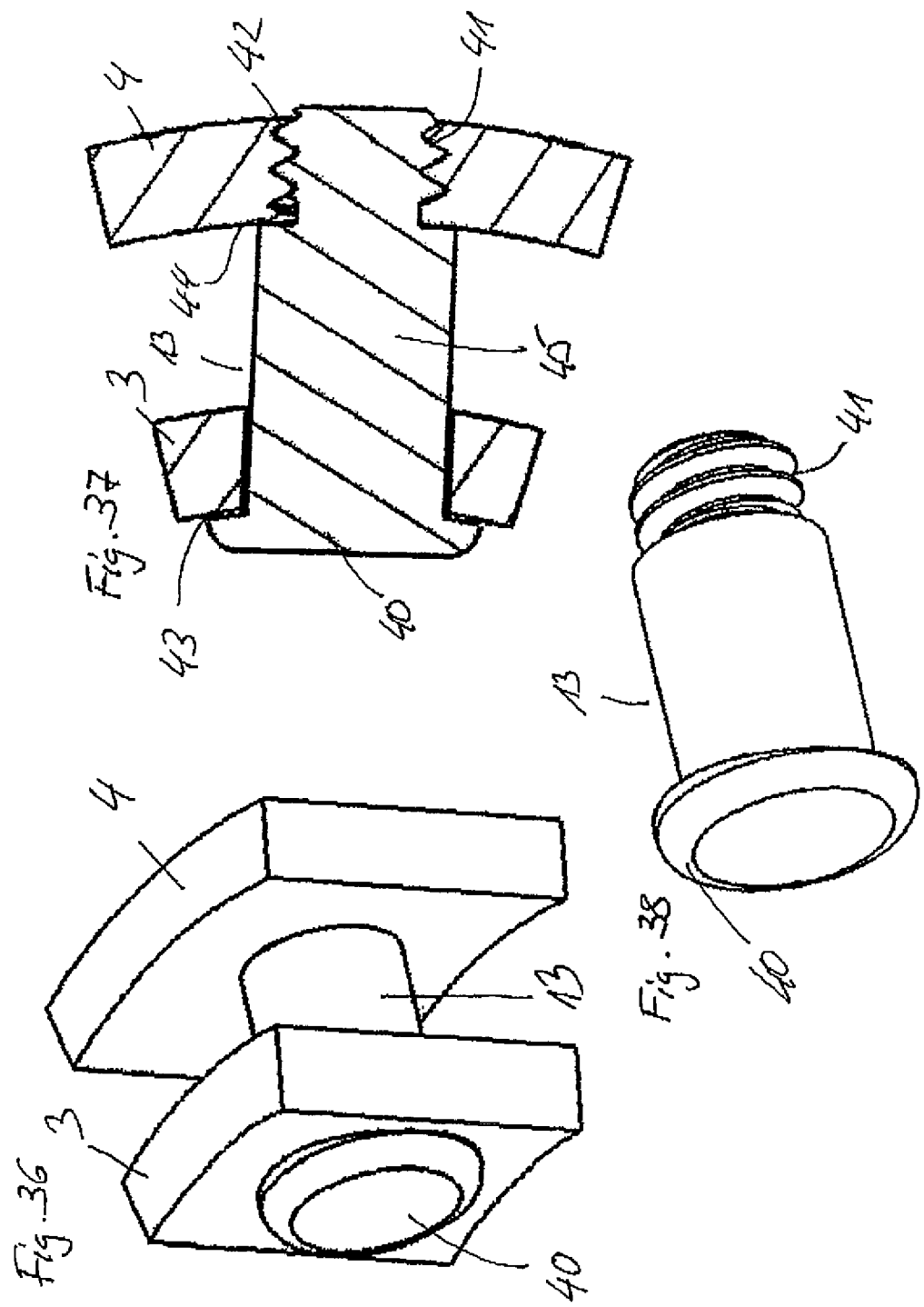

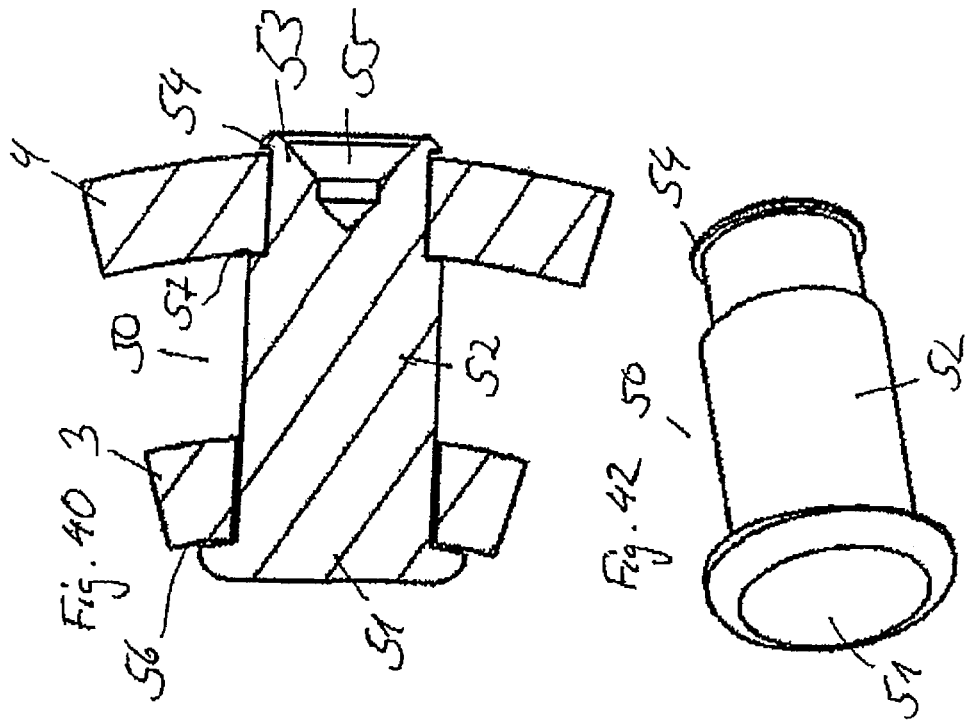
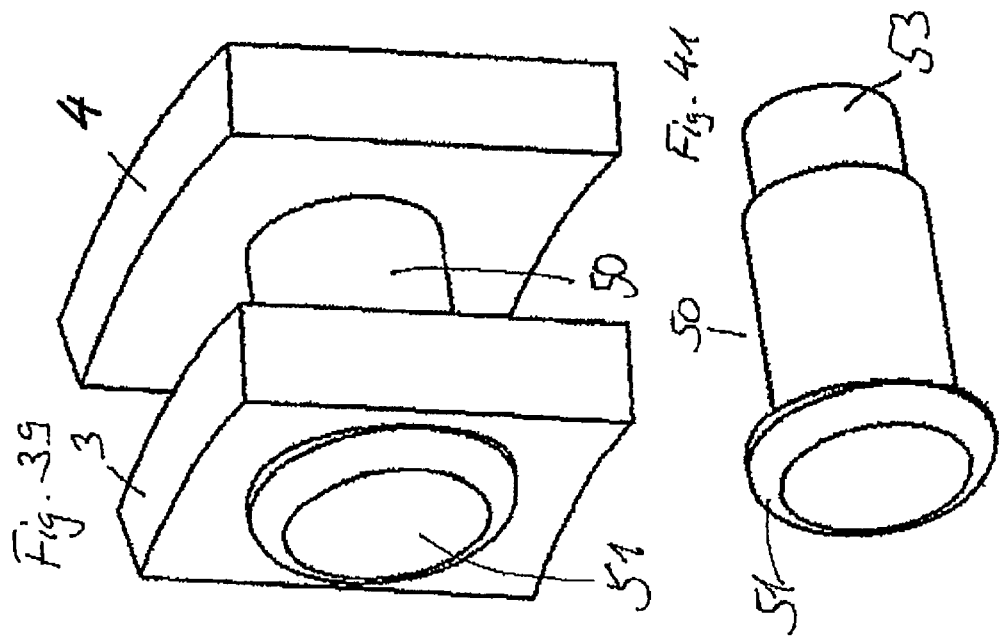

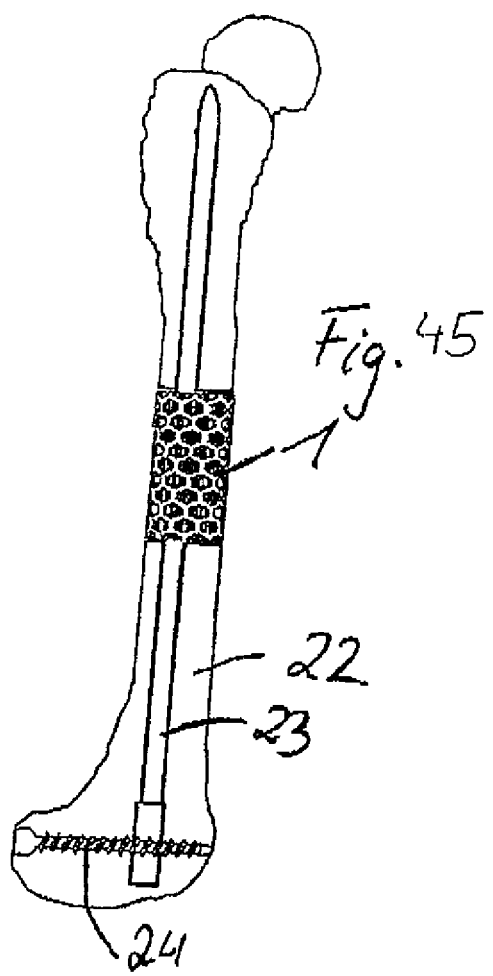

MULTI-WALLED PLACEHOLDER

CROSS-REFERENCE TO RELATED APPLICATION(S)

This application is a continuation of U.S. patent application Ser. No. 15/728,405, filed Oct. 9, 2017, which is a continuation of U.S. patent application Ser. No. 15/012,827, filed Feb. 1, 2016, now U.S. Pat. No. 9,814,595, which is a continuation of U.S. patent application Ser. No. 13/914,471, filed Jun. 10, 2013, now U.S. Pat. No. 9,254,199, which is a continuation of U.S. patent application Ser. No. 11/645,228, filed Dec. 22, 2006, now abandoned, which claims the benefit of and priority from U.S. Provisional Patent Application Ser. No. 60/753,854, filed Dec. 23, 2005, and the benefit of and priority from U.S. Provisional Patent Application Ser. No. 60/808,028, filed May 23, 2006, the disclosures of all of which are incorporated herein by reference.

BACKGROUND

The present invention refers to a placeholder for implantation into a human or animal body, especially as a placeholder for vertebrae or vertebral discs, a method for manufacturing such a placeholder, and a modular system for such a placeholder.

Placeholders, especially for vertebrae or vertebral discs are known. For example, DE 19504867 C1 discloses a placeholder in the shape of a cylindrical-tubular body with a plurality of rhombic or diamond-shaped openings that are arranged in rows and columns. At the ends of the cylindrical tube are provided projecting serrations and recesses in correspondence with the rhombi that serve for engaging with adjacent vertebrae or adjacent tissue. The diamond-shaped openings facilitate in-growth of the tissue into the implant, such that the latter may knit well with the body.

Moreover, an implant is known from US 2005/0015154 which has a scaffold-like structure in which the latticework extends over the full body or through the entire body of the implant. Such integral latticework structures are intended for use especially in replacement implants for joints, such as hips, knee joints, shoulder joints and the like. However, such integral latticework structures are difficult to manufacture and have to be adjusted and manufactured individually to suit every application case.

DE 101 38 079 A1 discloses a placeholder of adjustable axial length in which two sleeve-like parts are arranged adjustably inside one another, more precisely via a lever arrangement over which the parts are connected. Although this device facilitates very precise length adjustment, the lever arrangement is complicated to manufacture.

DE 198 04 765 C2 discloses a placeholder for insertion between two vertebrae with an adjustable axial length. The total length is adjusted by moving an external tube relative to an internal tube. The length adjustment proceeds stepwise by means of catches.

DE 697 19 431 T2 describes a longitudinally adjustable vertebral disc placeholder in which two sleeve bodies arranged telescopically inside one another are adjusted relative to each other and are lockable via screw arrangements. However, this arrangement does not uniformly distribute the load across the screw connections and does not effectively allow in-growth by the surrounding tissue because of the close arrangement of the sleeve bodies.

US 2003/0078660 discloses an implant that may be used as a placeholder in which the implant has a sleeve-like body that is corrugated. This corrugated body may in turn be arranged inside a further sleeve body. However, the corrugated form of the one implant part again makes for complicated manufacture.

EP 09 047 51 A1 describes a tubular support body for vertebrae having two cages guided in one another which may be connected to each other by a projecting stud on the jacket surface of the one cage and axial feed channels in the jacket of the other cage. With this arrangement, facilitating of latching positions at different depths is provided. However, the support body is limited in variability by the feed channels.

Based on the above, there is a need for an implant which is easy to manufacture and versatile in use, can provide load dissipation, allows in-growth into human or animal tissue, and is suitable for use as placeholder in the spine, that is, for vertebral discs and vertebrae, but also for tubular bones of the upper and lower extremities.

SUMMARY

According to one aspect of the present invention, several tubular bodies, namely a first tubular body and at least a second tubular body, are provided at least partially one inside the other, such that a multi-wall placeholder is formed which not only provides load-absorbing properties but also is suitable for allowing in-growth of adjacent tissue. The cross-sectional shapes of the first and the second bodies in a cross-sectional plane transverse to the longitudinal axis of the placeholder can be different. In particular, the second body arranged in the first body can have a simple or basic geometric shape, namely, a shape which is easy to manufacture. Such shapes include cylindrical or cuboid shapes with round, oval, rectangular or triangular cross-sections. In addition, a shape having a constant cross-section along its length may be used. Such simple geometrical basic shapes for the first and second bodies may be used to generate suitable mechanical properties, yet are affordable and easy to manufacture.

The multi-wall placeholder described herein also provides a large contact surface with the bone at the front face of the placeholder. In addition, with a preassembled multi-wall placeholder, a better adjustment to the bone is possible. Consequently, subsidence of the placeholder may be considerably reduced, if not completely prevented. This can be important for weak osteoporotic vertebrae. The placeholder according to the present invention may also include a plurality of second tubular bodies nested inside each other, all of which are at least partially disposed in the first tubular body.

In one embodiment, the first body may have a circular cross-sectional shape, while the second body or bodies may have a triangular, square, hexagonal, octagonal or generally polygonal, oval or kidney cross-sectional shape.

In a further embodiment, the first tubular body, i.e., the external body may have a cross-sectional shape other than that of a circle, such as an oval or kidney cross-sectional shape, in which case the second body may have a correspondingly adjusted different cross-sectional shape, as described above or a similar shape.

According to another aspect of the present invention, which is also applicable to all disclosed aspects of the invention, several second bodies may be arranged alongside each other in the first body. Accordingly, this arrangement can also achieve mechanical stability and/or ease of in-growth by the surrounding tissue into the placeholder. In addition, the wall thicknesses of the individual components, i.e. of the tubular bodies, may be kept small so as to facilitate in-growth of the tissue into the tubular bodies and thus into the implant.

By providing several second bodies in the first body, e.g., two or three second bodies, the wall thickness of the individual tubular bodies can be reduced, while the overall loading capacity can be improved. The arrangement of two, three or several second bodies in the first body is applicable to all disclosed aspects of the invention.

The second bodies can be spaced from each other and/or from the first body to promote in-growth of body tissue between the bodies. This also allows for more precise adjustment relative to the adjacent bone or to a placeholder end plate. Moreover, the spacing between the bodies will result in better in-growth and a more homogeneous distribution of the load across the cross-section of the implant.

In the case of the arrangement of several second bodies in the first body, the arrangement of the second bodies may be such that their longitudinal axes are offset parallel to the tubular longitudinal axis of the first body. The result of this is that greater stability can be obtained for certain instances of mechanical loading. For example, the offset arrangement of the bodies may lead to greater stability in the case of flexural stress.

Overall, the cross-sectional shape of the first and/or second bodies may assume diverse shapes, namely circles, triangles, oblongs, rectangles, squares, diamonds, (rhombi), polygons, hexagons, octagons, especially with rounded corners, ovals, kidney shapes or any free-form shapes. However, the shape can be restricted to certain basic shapes as this simplifies manufacturability. Among the basic shapes are especially circles, triangles, oblongs, rectangles, squares, diamonds, hexagons, all angular shapes including those with rounded corners and ovals and kidney shapes.

According to a further aspect of the present invention, which is also applicable to all disclosed aspects of the invention, the second body or bodies can be accommodated in the first body by means of a press fit or force fit. For example, the outer dimension of the second body or bodies is larger than the inner dimension of the first body. This results in an elastic deformation of the bodies in the case of a force fit or an additional plastic deformation in the case of press fit. Alternatively, a connecting element or retaining element between the bodies can be a force fit or press fit.

The press fit or force fit may be directly affected by contact between the first body and the second body/bodies or by the connecting elements.

Alternatively, according to a further aspect of the invention, the connections between the bodies and/or connecting elements may take place by means of friction, a material or a positive connection (form-fit).

According to another aspect of the present invention, which is also applicable to all disclosed aspects of the invention, the placeholder comprises a first tubular body having a jacket surface with a plurality of openings for over-growth with adjacent tissue and a second tubular body having a jacket surface with a plurality of openings, the second tubular body disposed at least partially inside the first tubular body. At least one spacer may be used wherein the second tubular body is spaced apart with the at least one spacer from the first tubular body. The spacer may also take the form of a connecting element configured to connect the first tubular body to the second tubular body.

In particular, the connecting elements may comprise retaining plates and/or connecting pins.

The retaining plates may be formed as plates or rings arranged transversely to the tubular longitudinal axis that are held by press fit or force fit or screw or rivet connections or generally by means of friction, a material or a positive connection (form-fit) in the first body. The second bodies may preferably also be held by press fit or force fit or again by connecting pins or generally by means of friction, a material or a positive connection.

This means that the second bodies, for example may form a structural unit with the connecting elements, which is then held overall by means of a press fit or force fit in the first body.

The connecting pins may be formed as rivets, screws and/or bars, which are welded, for example.

For arranging the second bodies in the first body, at least one, but preferably several, and especially two retaining plates may be provided. The arrangement of the retaining plates may occur at the ends of the tubular bodies as end plates or distributed along the length of the tubular bodies as intermediate plates.

The retaining plates may have a plurality of openings as well, more precisely in addition to the receivers, by means of which the second bodies are received and held. The plurality of openings again serves the purpose of in-growth of adjacent tissue.

In addition or as an alternative to the retaining plates, connecting pins may be provided, which are formed especially as rivets, screws and/or bars, which are, for example, welded.

The connecting pins preferably have stop faces for spaced retention of the bodies, for example a stop face may be provided by a corresponding rivet or screw head, while a second stop face may be provided in the vicinity of the thread or of the end of the rivet opposite the head.

The connecting pins may be arranged in the openings or breakthroughs in the jacket surface of the tubular bodies which are provided for knitting with adjacent tissue. Alternatively, separate connecting openings may be provided for receiving the connecting elements in the tubular bodies or other components of the implant, such as the retaining plates.

In the case of screw connections, preferably the thread holes are provided in the first outer body, such that the screw with its screw head lies on the inside. This results in a smooth external side without projections parallel to the tubular longitudinal axis.

According to a further aspect of the invention, which is also applicable to all disclosed aspects of the invention, the tubular bodies can be arranged at least partially inside each other and may be connected by means of detachable connecting means or connecting means attachable or connectable directly at the point of use, such that a modular system is created, which facilitates in simple fashion individual adjustment to requirements. Accordingly, a modular system of several tubular bodies and corresponding connecting means may be provided, with the surgeon composing the corresponding placeholders to suit individual needs directly at the point of use. Naturally, however, the placeholders may also be supplied ready-made. But, even here, changes may still be made in the case of detachable connecting means.

Additionally, a connection of the tubular bodies can be provided merely at a few sites on the jacket surface and/or in the vicinity of the front faces, such that, when viewed along the full length of the placeholder, free space that is available for in-growth of tissue is created in wide areas between the placeholders. For example, the connecting elements may be restricted to a total of 2 to 24, preferably 2 to 12 elements, and/or 2 to 4, especially 3. In another embodiment, three connecting elements may be assigned to each row of openings or breakthroughs in the jacket surface. The connecting elements may cooperate with the breakthroughs themselves or with further receivers, recesses or holes, such as thread holes.

In a further embodiment, the tubular bodies may be arranged concentrically, such that parallel wall areas are formed, especially in the case of the same cross-sectional shapes.

In yet another embodiment also applicable to all disclosed aspects of the invention, the connecting elements may preferably be variably attached in the openings of the jacket surface of the tubular bodies, such that the tubular bodies may be arbitrarily aligned and arranged relative to each other. For example, the bodies can be arranged such that they are not completely inside each other, but to, for example, leave them projecting out in the longitudinal direction. This means that the length or height of the placeholders may be adjusted, since the different tubular placeholders arranged inside one another may be retracted telescopically from each other or, conversely, pushed into each other in order for them to be subsequently fixed in this position. This is especially possible continuously or in steps. Additionally, the tubular bodies may also be rotated against each other, such that the openings provided in the jacket surfaces are in alignment or staggered relative to, for example, one or two adjacent bodies or all bodies.

Also, the tubular bodies may have different forms, especially different wall thicknesses, such that, for example, the external tubular body may be very thin in order to facilitate rapid over-growth or in-growth by the surrounding tissue through the openings, while the internal body or bodies have a greater wall thickness to impart stability to the placeholder.

The different shapes which are possible for the cross-sectional shapes are also conceivable for the openings or breakthroughs in the jacket surface of the tubular bodies, such that their external contour, too, may have the shape of a circle, a triangle, an oblong, a rectangle, a square, a hexagon, an octagon, generally a polygon with or without rounded corners, a diamond or similar.

In all aspects, the tubular bodies may be arranged spaced apart from each other, with this space either provided by the connecting elements that connect the tubular bodies and/or separate spacers that may be provided, especially on the inside and/or outside of the jacket surface, preferably in the shape of bars or plates projecting at right angles towards the outside or the inside. On account of the spacing of the tubular bodies, sufficient space is available for in-growing tissue. Furthermore, on account of the spaced arrangement of tubular bodies, correspondingly broad contact surfaces may form at the ends or front faces that render separate attachment of end plates or similar unnecessary.

The tubular bodies may also have, at least on one end, or on both ends, projections and/or recesses which enable engagement with adjacent vertebrae or other tissue and facilitate in-growth.

The connecting elements, which may be formed by pins, bolts, catches, screws, end plates and similar, may be variably accommodated, especially at the openings or breakthroughs of the jacket surface, such that no additional separate receivers need to be provided for the connecting elements. This can reduce outlay and simplifies manufacturability. Nonetheless, corresponding separate receivers may be provided at the jacket surfaces of the tubular bodies.

In a further embodiment, the placeholders have, at the front faces of the tubular bodies, at least one, preferably two end plates, which simultaneously serve as connecting means. The end plates, which, for example, are annular, have for this purpose cut-outs and/or recesses into which the projections at the ends of the tubular bodies may engage, especially positively and/or non-positively. The annular end plate may function as a tensioning or spring-loaded ring that has a separating gap or slit, such that the projections provided in the cut-outs or recesses of the tubular bodies are held by means of friction by the end plate.

Correspondingly, the intermediate plates or retaining plates may also be formed generally as tensioning or spring-loaded rings.

Alternatively or additionally, it is naturally also possible to have a bonded (material) connection of end plates or retaining plates and tubular bodies, such as by means of welding, especially laser welding, as also applies to the other connecting means, especially those provided in the vicinity of the jacket surfaces, The tubular bodies and/or the connecting elements may be coated or have received a surface treatment. For example, coatings to be mentioned in this regard are hydroxy apatite or plasma treatments, which, for example, may lead to a rough titanium surface if titanium or titanium alloys are used as material.

Overall, all suitable biocompatible materials having the corresponding properties may be used for the various components, such as tubular bodies and connecting elements. Preferred are biocompatible polymers or metals, such as titanium or titanium alloys, or also nitinol, a nickel-titanium alloy. Especially, different materials may also be used for the various components.

According to a further aspect, the placeholder has at least two different tubular bodies, for example, one body differing in diameter from the other. These bodies are arranged at least partially inside each other, and the bodies are then connected to each other, preferably detachably, by means of at least one connecting element. In this regard, the arrangement of the tubular bodies may be varied relative to each other, e.g., along the longitudinal axis. This is especially true if the connecting elements may be used at many locations along the tubular bodies. Additionally, the angle arrangement between bodies may be varied.

Through the structure of the tubular bodies of the invention, which is described in detail especially in the following embodiments, it is also possible to adjust the length and/or the alignment of the ends of the tubular bodies by means of cutting to length at any site, The result is a further increase in the variability of use.

Additionally, the placeholders may be coated or subjected to surface treatment not only altogether following assembly, but also individually before the components are assembled. Accordingly, even in the case of parts on the inside, such as a cylindrical tubular body arranged lying on the inside, said body may be coated or surface treated prior to assembly, such that complete coating or surface treatment here may occur.

In another embodiment, the present invention provides a modular, individually usable system for placeholders, e.g., through the use of individual components, which can be used alone, preassembled or selectively assembled. The corresponding placeholder has an extremely large surface area due to its many walls and construction from several tubular bodies, and thus markedly facilitates in-growth and on-growth. Additionally, despite the very large surface area, manufacturability is improved and, in particular, coatability and surface treatability are improved. This also results in improved in-growth properties. In particular, the modular assembly allows for individual surface treatment of the single components. Thus, different coating of the individual components may take place, i.e., of the various cylindrical-tubular bodies located in the different positions. This results in an implant having good mechanical stability and improved in-growth characteristics, which is especially suitable for vertebral discs or placeholders. An optimum fusion element for orthopedics is thus achieved.

BRIEF DESCRIPTION OF THE DRAWINGS

Further, characteristics and features of the invention are apparent from the following description of preferred embodiments using the enclosed drawings. The drawings show in purely schematic form, in FIG. 1 a first embodiment of a placeholder of the invention;

FIG. 2 a plan view of the placeholder from FIG. 1;

FIG. 3 a three-dimensional representation of a further placeholder of the invention with a detailed representation of the jacket surface;

FIG. 4 a plan view of the placeholder from FIG. 3;

FIG. 5 a three-dimensional representation of a third embodiment of a placeholder of the invention;

FIG. 6 a plan view of the placeholder from FIG. 5;

FIG. 7 a perspective representation of the placeholder from FIG. 5 without end plate;

FIG. 8 a plan view of the placeholder from FIG. 7;

FIG. 9 perspective representations of two individual tubular bodies and the placeholder in the assembled state and plan views of the respective tubular bodies;

FIG. 10 a perspective view of a further embodiment of a placeholder of the invention with a detailed view of the jacket surface;

FIG. 11 a perspective representation of a further embodiment of a placeholder of the invention with a detailed view of the jacket surface;

FIG. 12 a perspective representation and a plan view of a further embodiment of a placeholder of the invention;

FIG. 14 perspective representation of a further embodiment of a placeholder of the invention;

FIG. 15 perspective representation of the embodiment of the placeholder from FIG. 14 in a shorter variant;

FIG. 16 a plan view of the placeholder in accordance with FIG. 15;

FIG. 17 a perspective representation of a further embodiment of the placeholder of the invention;

FIG. 18 a plan view of the placeholder from FIG. 17;

FIG. 19 a perspective representation of a further embodiment of a placeholder of the invention;

FIG. 20 a plan view of the placeholder from FIG. 19;

FIG. 21 a perspective representation of a further embodiment of a placeholder of the invention;

FIG. 22 a plan view of the placeholder from FIG. 20;

FIGS. 25 to 29 representations of cross-sectional shapes of tubular bodies for the present invention;

FIGS. 30 to 35 representations of the shapes of breakthroughs or openings in the jacket surface of a placeholder or tubular body of the invention;

FIG. 36 a perspective representation of a screw connection;

FIG. 37 a cross-sectional view of the screw connection from FIG. 36;

FIG. 38 a perspective view of a connecting pin as screw;

FIG. 39 a perspective view of a rivet connection;

FIG. 40 a cross-sectional view of the rivet connection from FIG. 39;

FIG. 41 a perspective representation of the rivet from FIGS. 39 and 40 in the un-riveted state;

FIG. 42 a perspective representation of the rivet from FIG. 41 in the riveted state;

FIG. 45 a lateral view of a third application example for the present invention.

DETAILED DESCRIPTION

Figure 13A:
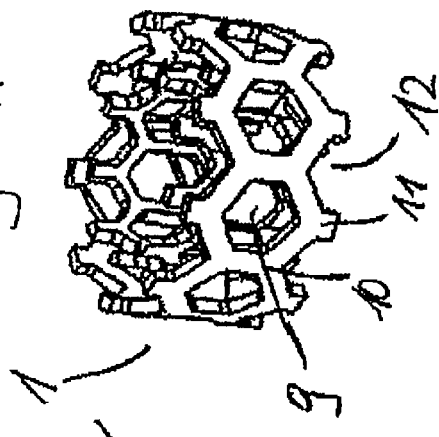
FIGS. 13 (a)-(c) a perspective representation, a lateral view and a plan view, respectively, of a further placeholder of the invention.

FIG. 1 shows a perspective representation of a first embodiment of a placeholder 1 of the invention in which the tubular bodies 2, 3 and 4 are partially arranged inside each other.

The tubular body 4, which has the largest diameter, accommodates the tubular bodies 2 and 3 of smaller diameter. Tubular body 3, which has the next largest diameter, accommodates the tubular body 2 of the smallest diameter.

The tubular body 3 is arranged in the tubular body 4, such that it projects over the edge 5 of the tubular body 4 in the direction of the longitudinal axis of the placeholder 1. Similarly, the tubular body 2 is arranged in the tubular body 3, such that it projects over the edge 6 of the tubular body 3.

The tubular bodies 2, 3 and 4 are connected to each other via pins 8 (see FIG. 2), which are detachably inserted by press fit through cut-outs or holes 25 (see FIG. 3) of the tubular bodies 2, 3, 4. Accordingly, it is possible, when the pins 8 have been removed, to adjust the length or height of the placeholder 1 by mutually pushing the tubular bodies 2, 3, 4 against each other along the longitudinal axis of the placeholder 1. At the desired length or height, the tubular bodies 2, 3, 4 may be attached to each other and fixed in the corresponding position by inserting the corresponding pins 8 into the holes 25.

The pins 8 may have corresponding stopping and/or catching means at their ends, such as hooks (not shown), to ensure that pins 8 are secured in the holes 25. Additionally, other connecting means, such as screws with threaded holes and the like, are conceivable.

The tubular bodies 2, 3, 4 have at their jacket surface 10 a plurality of openings 9, which in the embodiment shown in FIG. 1, have a hexagonal shape and are uniformly arranged in rows and columns, such that a generally honeycomb structure is produced. On account of this honeycomb structure, simple in-growth of tissue is ensured combined with simultaneous stability and strength of the placeholder 1. Additionally, the weight of the placeholder 1 is reduced. Due to the multiple wall formation on account of the arrangement of tubular bodies 2, 3 and 4 inside each other, in-growth of tissue is not hampered at least in the overlapping regions despite increased stability and strength.

FIGS. 3 and 4 are a perspective representation (FIG. 3) and a plan view (FIG. 4) of a further embodiment of a placeholder 1 in accordance with the invention, in which similar or identical parts are provided with the same numerals.

The embodiment of FIGS. 3 and 4 differs from that of FIGS. 1 and 2 essentially in that the tubular bodies 2, 3 and 4 are completely accommodated inside each other such that the tubular bodies 2 and 3 do not project beyond the upper edge 5 of the tubular body 4.

As a result, the edges 7, 6, 5 of the tubular bodies 2, 3 and 4 form a common contact plane for, e.g., an adjacent vertebra. Due to the three tubular bodies 2, 3 and 4 being arranged inside each other, and being spaced apart from each other, the result as compared to a single tubular body, is a much greater contact surface in the form of a ring, without the need to provide additional end plates or the like.

The ends of the tubular bodies 2, 3 and 4 of the embodiments of FIGS. 1 to 4 each have projections in the form of projecting bars or spikes 11 (referred to herein as projections 11) and indentations 12, such that overall corrugated edges 7, 6 and 5 result. The projections 11 and the indentations 12 can be made by cutting off or cutting to length the structure of the tubular bodies 2, 3 and 4 perpendicular to the longitudinal axis, and more precisely approximately in the middle of a series of openings 9. Correspondingly, each indentation 12 has a shape with parallel wall sections formed by the projections 11 and a triangular bottom, which connects the parallel wall sections.

The projections 11 and the indentations 12 engage with adjacent body parts, such as vertebrae or adjacent tissue and permit over-growth with corresponding tissue.

Moreover, the detailed representation of FIG. 3 shows the holes 25 or receivers for the pins 8 for connection of the tubular bodies 2, 3, 4. Instead of the pins 8 and holes 25, screws and threaded holes could also be used.

In FIG. 4, it may be seen that the concentrically arranged tubular bodies 2, 3 and 4, which are each formed as a cylinder in the embodiments of FIGS. 1 to 4, are spaced apart from each other and held by individual, thin bars 13, which, in turn, are radially spaced apart from each other by a certain angle. In the embodiment shown in FIG. 4, the bars 13 are radially spaced apart from each other by an angle of 120°.

In contrast to the pins 8, which may be detachable and/or attachable directly during the surgery involving the placeholder 1 of the embodiments of FIGS. 1 and 2, the bars 13 may have a solid bonded connection (material connection) for example by means of laser welding, with the tubular bodies 2, 3 and 4, such that the placeholder is ready-made.

FIGS. 5 to 8 show in various representations a further embodiment of a placeholder 1 in accordance with the invention, which, like the embodiments of FIGS. 1 to 4, may especially be used as placeholders for vertebrae. Here, too, identical or similar components are provided with the same reference numerals.

The embodiment of FIGS. 5 to 8 has, as especially shown by FIG. 8, two tubular bodies 3 and 4, which are arranged with tubular body 3 completely accommodated in the tubular body 4.

The embodiment of FIGS. 5 to 8 differs from the embodiments of FIGS. 1 to 4 in that, at each of the upper and lower ends, an end plate 14 in the shape of an annular disc is provided, which is subdivided by a slit or gap 16. Moreover, several rectangular cut-outs 15 are arranged annularly in the end plate 14. Accordingly, as particularly shown from the plan view of FIG. 6, the cut-outs 15 accommodate the projections 11 of the tubular bodies 4 and 3.

Due to the slit 16, the annular end plate 14 functions as a tensioning or spring-loaded ring. For example, the width of the gap 16 can be elastically reduced by squeezing the ends 17 and 18 together when the end plate 14 is arranged. Due to the elastic recovery forces of the annular end plate 14, on being released after placement on the tubular bodies 3 and 4 and the insertion of the projections 11 into the cut-outs 15, the end plate 14 relaxes, with the projections 11 being squeezed and pressed against the edges of the cut-outs 15. Thus, the end plate 14 is held against the projections 11 non-positively or by friction.

Support of this kind is also possible for retaining plates that are not arranged at the ends of the tubular bodies but positioned along the length of the tubular bodies at locations intermediate the ends of the tubular bodies.

FIGS. 7 and 8 show the placeholder 1 of FIGS. 5 and 6 in a representation without the end plates 14. Here it may be seen that the tubular bodies 3 and 4 are kept spaced apart merely on account of the end plates, without the need for additional connecting elements or spacers.

FIG. 9 shows a further embodiment of a placeholder 1 in accordance with the invention, with the tubular bodies 3 and 4 initially shown individually and, in the right sub-figure, in the assembled state. Aside from the perspective representations, the lower part of FIG. 9 shows the plan views of the tubular bodies 3 and 4. Again, identical or similar components are provided with the same numerals, as in the previous embodiments.

While the external tubular body 4 essentially corresponds to the previous embodiments, the inner tubular body 3 additionally has spacers 19 in the form of plates, which project perpendicularly outwards in several rows on the jacket surface 10 of the tubular body 3. The spacers 19 may either be formed integrally with the cylindrical body 3 or attached to it by means of bonded (material), positive (form-fit) or non-positive (frictional) connection, Naturally, it is also conceivable for the spacers 19 to be similarly provided on the inside of the external tubular body 4 or on both tubular bodies 3 and 4.

The individual spacers 19 are radially spaced around the circumference of the tubular body 3 at a specific angle, more precisely, in the embodiment shown in FIG. 9, each at an angle of 40°. Naturally, more or fewer spacers 19 may be arranged around the circumference or in a row, more or fewer rows and also at different distances.

In the embodiment shown, the spacers 19 may also be used simultaneously as connecting elements between the tubular bodies 3 and 4, for example by corresponding catch, interlocking or clip connections. This is possible, for example, if corresponding cut-outs are provided on the inside of the tubular body 4 into which the spacers 19 may engage. For example, the dimensions of the inner diameter of the tubular body 4 and the outer diameter of the tubular body 3 with the spacers 19 may be designed such that the outer diameter of the tubular body 3 with the spacers 19 is slightly greater than the inner diameter of the tubular body 4, such that one or both of the bodies 3 and 4 is elastically extended or compressed, respectively, during assembly and relaxation then occurs when the spacers 19 engage with the corresponding cut-outs or recesses (not shown) on the inside of the tubular body 4 in order to simultaneously act as connecting elements.

FIGS. 10 and 11 show further embodiments of placeholders in accordance with the invention, and find application, for example, in the case of or for replacing vertebral discs. Here again, identical or similar parts are provided with the same numerals.

FIGS. 10 and 11 illustrate especially by way of the enlarged detailed views of the jacket surface 10 that the tubular bodies 3 and 4 may be aligned differently, more precisely on the one hand such that the openings 9 are flush or aligned with each other, as shown in FIG. 11, or, offset, as shown in FIG. 10. In an offset arrangement of the openings 9, the bar-like regions of the mantle jacket 10 of the inner tubular body 3 may be seen behind the opening 9 of the external tubular body 4, whereas the bar-like regions of the jacket surface $10^4$ of the external tubular body 4 partially cover the opening of the tubular body 3.

In contrast, in the case of the flush alignment of openings 9 of the tubular bodies 3 and 4, the jacket surface region $10^3$ of the inner tubular body 3 is arranged behind the jacket surface region $10^4$ of the external tubular body 4 and a through-opening 9 is created in the jacket surfaces 10 of the bodies 3 and 4.

FIG. 12, in turn, shows a placeholder for vertebrae that essentially corresponds to the previous embodiments and thus has the same numerals for identical or similar components.

In the placeholder 1 of FIG. 12, the tubular bodies 2, 3 and 4 are again inserted in each other, the particular feature here being that the tubular bodies 2, 3 and 4 have different wall strengths or thicknesses, as is especially evident in the plan view in the right sub-figure of FIG. 12. Thus, the inner and outer tubular bodies 2 and 4 are thinner than the central tubular body 3. Thus, the central tubular body 3 contributes the most to strength and stability, while the outer and inner tubular bodies 4 and 2 facilitate rapid in-growth and overgrowth due to the low wall thickness. Spacers, such as pins 8 or bars 13, are not shown herein for illustration purposes.

Figure 13B:
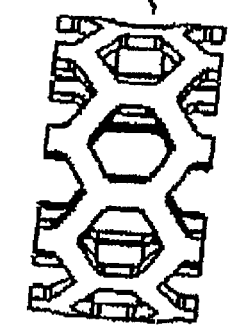
Figure 13C:
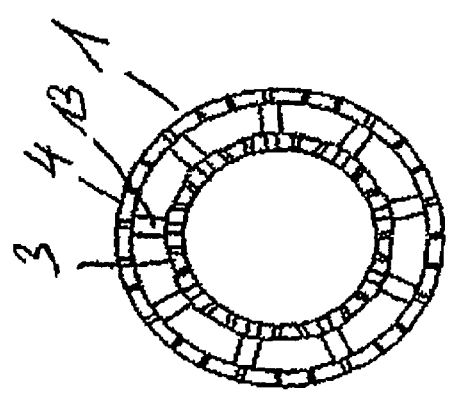

FIG. 13 shows in the three sub-views (a) to (c), a perspective view (a), a lateral view (b) and a plan view (c) of a placeholder 1 for a vertebral disc. Here, again, identical or similar components are provided with the same numerals, as in the previous embodiments.

The embodiment of FIG. 13 corresponds to the placeholder 1 of FIG. 3, the difference being that just two tubular bodies 3 and 4 are provided and that only a single row of completely formed openings 9 is provided. Correspondingly, the height or length of the placeholder 1 of FIG. 13 is markedly reduced relative to that of the placeholder 1 from FIG. 3. This corresponds to the different use purposes, namely on one hand to serve as placeholder for vertebrae (FIG. 3) and on the other to be used as placeholder for a vertebral disc (FIG. 13).

FIG. 14 shows in a further embodiment a perspective view of a placeholder in accordance with the invention in which again identical numerals are used for the same or similar components, as in the previous embodiments.

The placeholder 1 in FIG. 14 has a first, tubular body 4 with a cylindrical tubular shape, which in turn possesses a plurality of diamond-shaped openings 9, which are arranged in rows and columns to form a honeycomb structure. The diamond-shaped openings 9 are limited by bars 10, which, as in the previous embodiments, form projections 11 and recesses 12 at the upper and lower edge at the ends of the cylindrical tubular body 4.

In the external tubular body two retaining plates 30 are arranged, that are provided in the end regions of the tubular body 4. The retaining plates 30 are completely accommodated in the tubular body 4 and are held there by press fit or force fit. Correspondingly, the outer diameter of the retaining plates 30 is chosen somewhat larger than the inner diameter of the tubular body 4, such that the parts are elastically tensioned. Other suitable means to secure the retaining plates may also be used.

The circular, disc-shaped retaining plates 30 have a plurality of openings 31, which facilitate in-growth and permeation by tissue.

Additionally, receiving openings 32 are provided in which second, cylindrical-tubular shaped bodies 3', 3" and 3''' are accommodated, which in their shape and form correspond to that of the external tubular body 4. However, the second tubular bodies 3', 3" and 3''' differ with regards to their dimensions, i.e. the diameter of the second tubular bodies 3', 3" and 3''' is chosen much smaller than that of the external tubular body 4. The receiving openings 32 of the retaining plates 30 are arranged at the corner points of an imaginary triangle (shown in FIG. 16 with dashed lines), such that the second tubular bodies 3', 3" and 3''' are accommodated side by side to each other in the interior space of the external tubular body 4. The tubular longitudinal axes of the second tubular bodies 3', 3" and 3''', which run through the center of the circular cross-section of the second tubular bodies 3', 3" and 3''', are therefore offset parallel to the longitudinal axis of the external tubular body 4.

The second tubular bodies 3', 3" and 3''' are also accommodated by press fit or force fit in the receivers 32 of the retaining plates 30. The outer diameter of the second tubular bodies 3', 3" and 3''' is thus again chosen somewhat greater than the diameter of the receiving openings 32, such that, on insertion of the second tubular bodies 3', 3" and 3''', elastic deformation of the second tubular bodies 3', 3" and 3''' and of the retaining plates 30 occurs, which effects the press fit of the tubular bodies 3', 3" and 3''' in the receiving openings 32.

While the embodiment of FIG. 14 may be used as a placeholder for vertebrae, the variant shown in FIG. 15, also in a perspective representation, is intended as a replacement for vertebral discs. Correspondingly, the placeholder 1 of FIG. 15, in which again identical or similar components are provided with identical numerals as in the previous embodiments, is chosen much smaller in length. Correspondingly, only a single retaining plate 30 is provided, instead of the two retaining plates of the embodiment of FIG. 14. The retaining plate 30 in the embodiment of FIG. 15 is arranged approximately in the middle of the height of the placeholder.

Other than the differences described herein, the embodiment of FIG. 15 does not differ from that of FIG. 14.

FIG. 16 shows a plan view of the embodiment of FIG. 15 in which the arrangement of the external tubular body 4 and of the second, inner tubular bodies 3', 3" and 3''' is clearly shown. Further, the openings 31, which are provided in the retaining plates 30 for in-growth and permeation by tissue, are shown. The openings 31 may have different sizes as shown.

Overall, with the embodiments of FIGS. 14 to 16, an implant or placeholder is provided which, on account of the chosen press fit or force fit arrangement, is readily manufacturable and whose components facilitate simple and variable arrangement. Additionally, sufficient free space for in-growth by tissue to the external tubular body 4 is provided by the arrangement of the tubular bodies 3', 3", and 3'''. At the same time, however, sufficiently large contact surfaces on the ends of the placeholder 1 are provided for accommodating and dissipating load.

FIGS. 17 to 24 show different embodiments in which, without use of a retaining plate, several or individual second tubular bodies 3 of different shapes are accommodated in differently shaped external tubular bodies 4, again by press fit or force fit.

In the embodiment which, in FIGS. 17 and 18, is shown in perspective and plan view representations, respectively, the external tubular body 4 has, in a cross-sectional plane perpendicular to the tubular longitudinal axis, i.e. perpendicular to the jacket surface, a kidney shape, whereas the second tubular bodies 3', 3" and 3''' accommodated in the external tubular body 4 have a circular cross-section. Correspondingly, the second tubular bodies 3', 3" and 3"' are accommodated side by side to each other in the external tubular body 4.

In the case of the placeholder 1, which, in FIGS. 19 and 20, is shown in perspective and plan view representations, respectively, two cylindrical tubular bodies 3' and 3" which have a circular cross-section are arranged, also by press fit or force fit, in an external tubular body 4 with an oval shaped cross-section, whereas, in the embodiment of FIGS. 21 and 22, three second bodies 3', 3" and 3"' with cylindrical tubular shape, i.e. circular cross-section, are arranged in an external tubular body 4 having a cylindrical-tubular shape and thus also circular cross-section.

Figure 24:
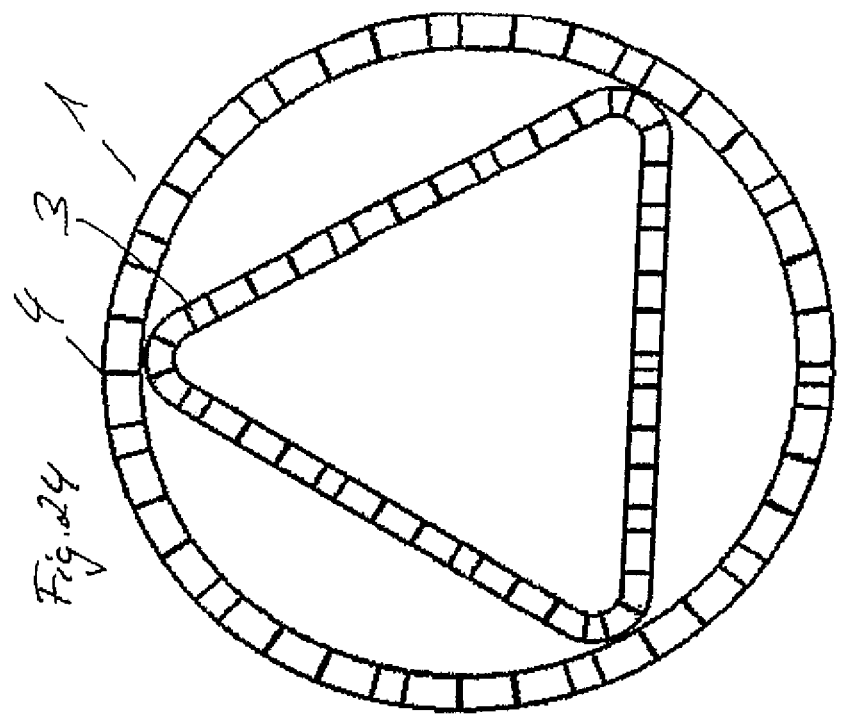
FIG. 24 a plan view of the placeholder from FIG. 23.
Figure 23:
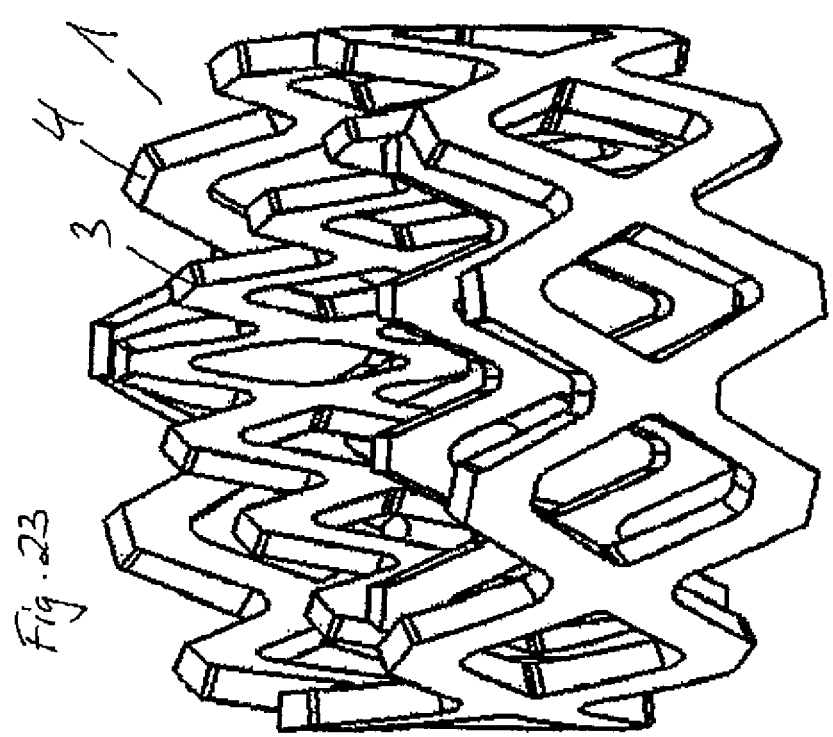
FIG. 23 a perspective representation of a further embodiment of a placeholder of the invention.

In FIGS. 23 and 24 is shown a further embodiment of a placeholder 1 in accordance with the invention in which, again, only two tubular bodies are arranged inside each other. In the embodiment shown in FIGS. 23 and 24, the inner tubular body 3 has a triangular shape in a cross-section running perpendicular to the tubular longitudinal axis, whereas the external tubular body 4, in turn, possesses a cylindrical tubular shape with circular cross-section. In the embodiment shown in FIGS. 23 and 24, thus only one tubular body 3 is accommodated by press fit or force fit in the tubular body 4.

In the variant shown in embodiments of FIGS. 17 to 24, it would also be possible, instead of press fit or force fit, to provide a connection for the first and second tubular bodies 4 and 3 at their contact surfaces by means of connecting elements, such as connecting pins in the form of screws or bonded (material) connections, such as welding.

FIGS. 25 to 29 show different cross-sectional forms of tubular bodies 2, 3, 4 of the kind that may be used in the present invention. Aside from a circular or annular cross-section, such as shown in FIG. 25, oblong, especially rectangular and preferably square shapes (FIG. 26), hexagonal shapes (FIG. 27), oval shapes (FIG. 28) or kidney shapes (FIG. 29) are conceivable. Additionally, there is the possibility of using other shapes, such as octagonal base shapes or totally free-form shapes. Preferred, however, are simple base shapes. Especially, it is also possible to combine cylindrical tubular bodies having different cross-sectional shapes with each other.

FIGS. 30 to 35 show different shapes of openings 9 and their mutual arrangement in the jacket surfaces 10 of the tubular bodies 2, 3 and 4. Aside from the diamond shape (rhombus) of FIG. 30, circular shapes (FIG. 31), oblong shapes, especially square and rectangular (FIG. 32), hexagonal shapes (FIG. 33), oval shapes (FIG. 34) or octagonal shapes (FIG. 35) are conceivable. Additionally, other suitable shapes are conceivable that facilitate a large area for the openings 9 combined with simultaneous stability of the interlaying framework.

As far as the mutual arrangement of the openings 9 is concerned, these may either be arranged in rows, in which the openings 9 are totally spaced apart in rows, such as in FIGS. 32 and 35, or the openings are arranged in the rows such that they project into the corresponding cavities formed by openings 9 of adjacent rows, as is particularly pronounced in the FIGS. 30 and 33.

This also shows that the openings 9 in the columns in which they are arranged may be provided directly beneath each other or, preferably, offset from each other, such that axial load dissipation, especially, improves. As FIGS. 30 to 35 further show, the columns with openings 9 arranged under each other may be each offset essentially from each other by the half-width of an opening.

FIGS. 36 to 42 show in different views embodiments of connections by means of connecting pins, such as rivets and screw connections.

FIG. 36 shows a partial section of the jacket surface 10 or of the bars forming the jacket surface 10 of tubular bodies 3 and 4, in which a screw connection is provided. The screw 13 has a screw head 40 which, as shown in a cross sectional view in FIG. 37, with a contact surface 43 makes contact with the inner surface of the tubular body 3, while the shaft 45 of the screw 13 projects through an opening in the wall of the tubular body 3 and with its screw end 41 opposite the head 40 engages with the threaded hole 42 of the external tubular body 4. In this connection, the contact surface 44, which limits the screw thread 41, makes contact with the inside of the external tubular body 4. The screw connection is designed such that preferably the outside of the tubular body 4 flushes with the thread-side end of the screw 13.

FIG. 38 shows the screw 13 in a perspective representation. Although not shown, the screw head may be configured to provide engagement with an actuating tool, such as a screw driver.

In similar representations as the screw connection, FIGS. 39 to 42 illustrate a rivet connection. Here, too, the rivet connection represents the connection between the tubular body 3 and the tubular body 4, as may especially be seen in the perspective representation of FIG. 39. With its contact surface 56, the head of the rivet 50 touches, as may be seen in FIG. 40, the inside of the tubular body 3, while the contact surface 57, which limits the rivet section at the end of the rivet 50 opposite the head 51, touches the inside of the external tubular body 4. The tubular bodies 3 and 4 each have one through-hole opening, through which rivet 50 with the rivet shaft 52 is inserted. The rivet area 53 has a cylindrically shaped cut-out 55, such that, following insertion of the rivet 50 through the through-hole opening of the tubular body 4, the edge 54 may be crimped such that a reliable connection is afforded and the rivet is prevented from leaving the through-hole opening of the tubular body 4.

FIGS. 41 and 42, each show the rivet 50 in the unriveted state (FIG. 41) and riveted state (FIG. 42) with edge 54.

Figure 44:
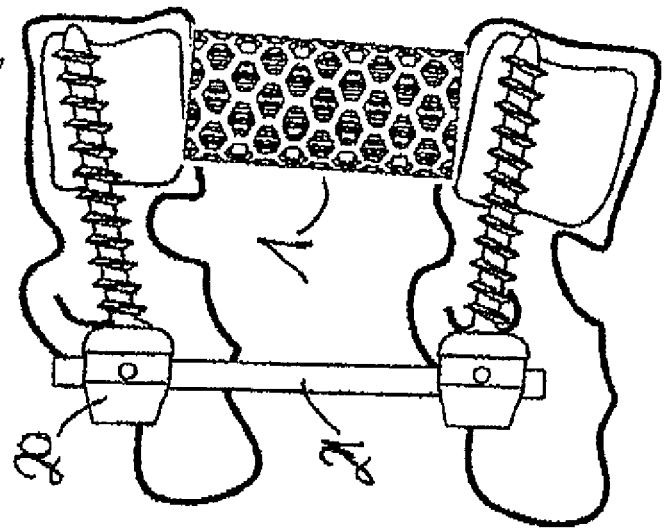
FIG. 44 a further schematic lateral representation of a further embodiment for the use of a placeholder of the invention.
Figure 43:
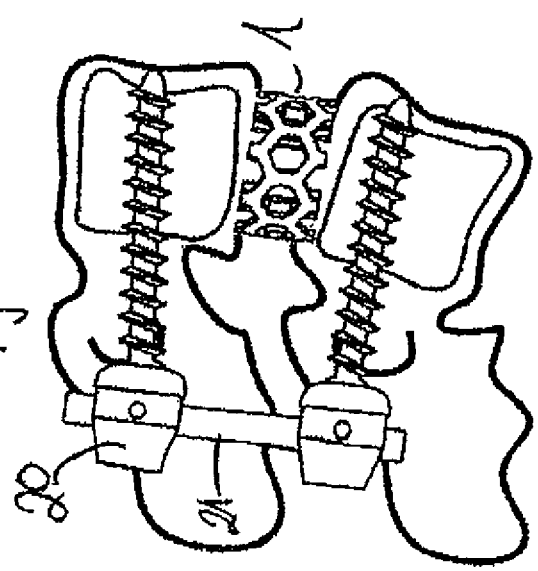
FIG. 43 a first example of a use of a placeholder of the invention in a schematic lateral representation.

FIGS. 43 to 44 are schematic lateral or sectional representations of applications for placeholders in accordance with the invention, with the placeholder 1 in FIG. 43 serving as a replacement vertebral disc and the placeholder 1 in FIG. 44 serving as a replacement vertebra.

The placeholders 1 in the applications of FIGS. 43 and 44 are part of a spinal column stabilization system, in which pedicle screws 20, especially polyaxial screws, are arranged in vertebrae, which accommodate between them a connecting rod 21 to mutually align and stabilize the spine.

Because of the arrangement in the spine, the placeholders 1 for the spine or vertebral discs are exposed to stresses, especially dynamic stress. The placeholder 1 according to the present invention, and in particular, the multi-wall configuration and/or the multi-component formation thereof, provides a solution for dealing with the noted stresses.

Additionally, the placeholder in accordance with the invention may also be used for clinical applications, such as long bones, e.g. following a break, as shown in FIG. 45, in which in case of destruction of the bone 22 in its central area, the arrangement of a corresponding placeholder 1 of the invention and stabilization with a nail 23 and a screw 24 may serve to reproduce the bone structure.

What is claimed is:

1. An implant for a human or animal body, the implant having a first end, a second end, and a longitudinal axis extending through the first and second ends, the implant comprising:
   a plurality of walls extending axially between the first and second ends, at least part of the plurality of walls being exposed to an outside of the implant, wherein a plurality of openings are defined by and extend laterally through each of the walls to promote in-growth of body tissue from outside the implant to the longitudinal axis;
   an outer frame comprising a first retaining structure that extends around the longitudinal axis at or near the first end and a second retaining structure that extends around the longitudinal axis at or near the second end, wherein each of the first and second retaining structures is connected directly to at least one of the walls for maintaining an overall structure of the implant;
   wherein an axial height of the entire implant is fixed and non-adjustable; and
   wherein each retaining structure is provided without openings that open laterally relative to the longitudinal axis, and extends farther from the longitudinal axis in each radial direction than an outermost one of the walls extends in the same radial direction.

2. The implant of claim 1, wherein the plurality of walls are arranged to define at least one inner cavity.

3. The implant of claim 2, wherein the inner cavity extends along the longitudinal axis and is open at both the first and second ends of the implant.

4. The implant of claim 2, wherein a cross-sectional profile of the inner cavity has substantially the same shape as, but is smaller than, a cross-sectional profile of the implant.

5. The implant of claim 1, wherein at least two of the plurality of walls are arranged concentrically around the longitudinal axis.

6. The implant of claim 1, wherein the first and second retaining structures each comprises a retaining plate.

7. The implant of claim 1, wherein the plurality of walls are recessed from the outer frame formed by the first and second retaining structures, and wherein multiple openings from among the plurality of openings are exposed to the outside of the implant between the first and second retaining structures.

8. The implant of claim 1, wherein at least one of the first or second retaining structures defines at least one open space that extends parallel to the longitudinal axis.

9. The implant of claim 1, wherein at least one of the walls extends axially past at least one of the first or second retaining structures in a direction away from other portions of the implant.

10. The implant of claim 1, wherein the implant is configured to be a vertebral implant, where the first and second ends are configured to contact vertebrae.

11. The implant of claim 1, wherein a head and a tip of a bone anchor are positioned along the longitudinal axis, with the plurality of walls of the implant extending between the head and the tip.

12. An implant for a human or animal body, the implant having a first end, a second end, and a longitudinal axis extending through the first and second ends, wherein an axial height of the entire implant is fixed and non-adjustable, the implant comprising:
   a plurality of walls extending axially between the first and second ends, wherein at least one opening is defined by and extends laterally through each of the walls to promote in-growth of body tissue;
   wherein at least two adjacent ones of the walls are at least partially recessed from an outer perimeter of the implant, have substantially the same structure, and extend parallel to one another in a direction of the longitudinal axis, wherein a connecting element extends between and connects at least part of the two adjacent walls, while an open space extends continuously between the first and second ends and separates at least another part of the two adjacent walls; and
   wherein at least one of the openings or the open space has an at least partially rounded or curved cross-sectional profile.

13. The implant of claim 12, wherein the implant defines at least one inner cavity.

14. The implant of claim 13, wherein the inner cavity extends along the longitudinal axis and is open at both the first and second ends of the implant.

15. The implant of claim 13, wherein a cross-sectional profile of the inner cavity has substantially the same shape as, but is smaller than, a cross-sectional profile of the implant.

16. The implant of claim 12, wherein the connecting element comprises a retaining plate.

17. The implant of claim 16, wherein at least one of the walls extends axially past the retaining plate in a direction away from other portions of the implant.

18. The implant of claim 12, wherein the implant is configured to be a vertebral implant, where the first and second ends are configured to contact vertebrae.

19. The implant of claim 12, wherein at least part of the plurality of walls is exposed to an outside of the implant.

20. The implant of claim 12, wherein each of the plurality of walls has a circular cross-sectional profile, and have longitudinal axes that extend parallel to one another and parallel to the longitudinal axis of the implant.

21. An implant for a human or animal body, the implant having a first end, a second end, and a longitudinal axis extending through the first and second ends, wherein an axial height of the entire implant is fixed and non-adjustable, the implant comprising:
   at least one cylindrical wall extending axially between the first and second ends, wherein a plurality of openings are defined by and extend laterally through the at least one cylindrical wall to promote in-growth of body tissue; and
   a retaining structure having at least a first portion provided without openings that open laterally relative to the longitudinal axis, wherein the first portion of the retaining structure is spaced apart from the first and second ends and contacts and extends 360° around an outside of the cylindrical wall;
   wherein the retaining structure is spaced apart from at least part of the outside of the cylindrical wall.

22. The implant of claim 21, wherein the cylindrical wall is tubular and defines an inner cavity that extends along the longitudinal axis.

23. The implant of claim 21, wherein the at least one cylindrical wall comprises a plurality of cylindrical walls that extend parallel to one another along the longitudinal axis of the implant.

24. The implant of claim 21, wherein the at least part of the outside of the cylindrical wall is exposed to an outside of the implant.

25. The implant of claim 21, wherein the retaining structure comprises a retaining plate.

26. The implant of claim 25, wherein the cylindrical wall extends axially past the retaining plate in a direction away from other portions of the implant.

27. The implant of claim 21, wherein the implant is configured to be a vertebral implant, where the first and second ends are configured to contact vertebrae.

28. The implant of claim 21, wherein a head and a tip of a bone anchor are positioned along the longitudinal axis, with the plurality of walls of the implant extending between the head and the tip.

29. The implant of claim 21, wherein at least one of the retaining structure or the cylindrical wall comprises titanium.

\* \* \* \* \*

UNITED STATES PATENT AND TRADEMARK OFFICE
CERTIFICATE OF CORRECTION

PATENT NO. : 11,083,589 B2
APPLICATION NO. : 16/166839
DATED : August 10, 2021
INVENTOR(S) : Lutz Biedermann It is certified that error appears in the above-identified patent and that said Letters Patent is hereby corrected as shown below:

On the Title Page

Item (73) Assignee, residence      Delete "Donaeuschingen" and insert -- Donaueschingen --.

In the Specification

Column 6, Line 16      Delete "surfaces," and insert -- surfaces. --.

Column 6, Line 45      Delete "site," and insert -- site. --.

Column 10, Line 30      Delete "connection," and insert -- connection. --.

Signed and Sealed this
Thirtieth Day of August, 2022

Katherine Kelly Vidal
*Director of the United States Patent and Trademark Office*